(12) United States Patent
Luzzio et al.

(10) Patent No.: US 6,964,961 B2
(45) Date of Patent: Nov. 15, 2005

(54) THIOPHENE DERIVATIVES USEFUL AS ANTICANCER AGENTS

(75) Inventors: Michael Joseph Luzzio, Groton, CT (US); Bingwei Vera Yang, Waterford, CT (US); Matthew Arnold Marx, Waterford, CT (US)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 09/873,555

(22) Filed: Jun. 4, 2001

(65) Prior Publication Data

US 2002/0042409 A1 Apr. 11, 2002

Related U.S. Application Data

(60) Provisional application No. 60/209,686, filed on Jun. 6, 2000.

(51) Int. Cl.[7] .................. C07D 495/04; A61K 31/4365
(52) U.S. Cl. .............................. 514/233.8; 514/253.04; 514/301; 544/127; 544/362; 546/114
(58) Field of Search ................................ 544/127, 362, 544/61; 546/114; 514/233.8, 253.04, 301, 228.2

(56) References Cited

U.S. PATENT DOCUMENTS

| 5,187,168 A | 2/1993 | Primeau ...................... 514/259 |
| 5,654,307 A | 8/1997 | Bridges et al. .............. 514/258 |

FOREIGN PATENT DOCUMENTS

| EP | 0071227 | 11/1987 |
| EP | 0364598 | 4/1990 |
| EP | 0452002 | 10/1991 |
| EP | 0778277 | 6/1997 |
| WO | 9317021 | 9/1993 |
| WO | 9519774 | 7/1995 |
| WO | 9640142 | 12/1996 |
| WO | 9713771 | 4/1997 |
| WO | 9729110 | 8/1997 |
| WO | 9823613 | 6/1998 |
| WO | WO 99/24440 | * 5/1999 |
| WO | 9924440 | 5/1999 |

OTHER PUBLICATIONS

Carmeliet and Jain, Angiogenesis in cancer and other diseases, Nature 407:249–257, 2000.*

* cited by examiner

*Primary Examiner*—Deepak Rao
(74) *Attorney, Agent, or Firm*—Steve T. Zelson; Garth Butterfield

(57) ABSTRACT

The invention relates to compounds of the formula 1

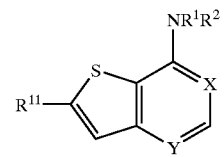

or a pharmaceutically acceptable salt and to pharmaceutically acceptable salts and hydrates thereof, wherein X, Y, $R^1$, $R^2$ and $R^{11}$ are as defined herein. The invention also relates to pharmaceutical compositions containing the compounds of formula 1 and to methods of treating hyperproliferative disorders in a mammal by administering the compounds of formula 1.

21 Claims, No Drawings

THIOPHENE DERIVATIVES USEFUL AS ANTICANCER AGENTS

This application claims the benefit of U.S. Provisional Application No. 60/209,686, filed Jun. 6, 2000, which is hereby incorporated by reference in its entirety.

BACKGROUND OF THE INVENTION

This invention relates to novel thiophene derivatives that are useful in the treatment of hyperproliferative diseases, such as cancers, in mammals. This invention also relates to a method of using such compounds in the treatment of hyperproliferative diseases in mammals, especially humans, and to pharmaceutical compositions containing such compounds.

Compounds that are useful in the treatment of hyperproliferative diseases are referred to the following patent applications: PCT international patent application number PCT/IB97/00675 (filed Jun. 11, 1997), U.S. provisional patent application No. 60/041846 (filed Apr. 9, 1997), U.S. provisional patent application No. 60/031862 (filed Nov. 27, 1996), U.S. provisional patent application No. 60/028881 (filed Oct. 17, 1996), PCT international patent application number PCT/IB97/00584 (filed May 22, 1997), U.S. patent application No. 08/653,786 (filed May 28, 1996), PCT international patent application publication number WO 96/40142 (published Dec. 19, 1996), PCT international patent application publication number WO 97/13771 (published Apr. 17, 1997), PCT international patent application publication number WO 95/23141 (published Aug. 31, 1995) and United States patent application having Ser. No. 09/502,129 (filed Feb. 10, 2000). Each of the foregoing United States and PCT international patent applications is incorporated herein by reference in its entirety.

It is known that a cell may become cancerous by virtue of the transformation of a portion of its DNA into an oncogene (i.e. a gene that upon activation leads to the formation of malignant tumor cells). Many oncogenes encode proteins which are aberrant tyrosine kinases capable of causing cell transformation. Alternatively, the overexpression of a normal proto-oncogenic tyrosine kinase may also result in proliferative disorders, sometimes resulting in a malignant phenotype.

Receptor tyrosine kinases are large enzymes that span the cell membrane and possess an extracellular binding domain for growth factors such as epidermal growth factor, a transmembrane domain, and an intracellular portion that functions as a kinase to phosphorylate specific tyrosine residue in proteins and hence to influence cell proliferation. The foregoing tyrosine kinases may be classified as growth factor receptor (e.g. EGFR, PDGFR, FGFR and erbB2) or non-receptor (e.g. c-src and bcr-abl) kinases. It is known that such kinases are often aberrantly expressed in common human cancers such as breast cancer, gastrointestinal cancer such as colon, rectal or stomach cancer, leukemia, and ovarian, bronchial or pancreatic cancer. Aberrant erbB2 activity has been implicated in breast, ovarian, non-small cell lung, pancreatic, gastric and colon cancers. It has also been shown that epidermal growth factor receptor (EGFR) is mutated or overexpressed in many human cancers such as brain, lung, squamous cell, bladder, gastric, breast, head and neck, oesophageal, gynecological and thyroid cancers. Thus, it is believed that inhibitors of receptor tyrosine kinases, such as the compounds of the present invention, are useful as selective inhibitors of the growth of mammalian cancer cells.

It has also been shown that EGFR inhibitors may be useful in the treatment of pancreatitis and kidney disease (such as proliferative glomerulonephritis and diabetes-induced renal disease), and may reduce successful blastocyte implantation and therefore may be useful as a contraceptive. See PCT international application publication number WO 95/19970 (published Jul. 27, 1995).

It is known that polypeptide growth factors such as vascular endothelial growth factor (VEGF) having a high affinity to the human kinase insert-domain-containing receptor (KDR) or the murine fetal liver kinase 1 (FLK-1) receptor have been associated with the proliferation of endothelial cells and more particularly vasculogenesis and angiogenesis. See PCT international application publication number WO 95/21613 (published Aug. 17, 1995). Agents, such as the compounds of the present invention, that are capable of binding to or modulating the KDR/FLK-1 receptor may be used to treat disorders related to vasculogenesis or angiogenesis such as diabetes, diabetic retinopathy, hemangioma, glioma, melanoma, Kaposi's sarcoma and ovarian, breast, lung, pancreatic, prostate, colon and epidermoid cancer.

SUMMARY OF THE INVENTION

The present invention relates to compounds of the formula 1

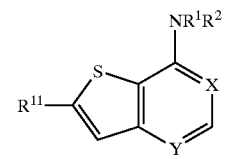

or a pharmaceutically acceptable salt, prodrug or hydrate thereof,

X is N, CH or C(CN);

Y is N, CH, CF, or N→O;

$R^1$ is H or $C_1$–$C_6$ alkyl;

$R^2$ is 5 to 13 membered heterocyclic, wherein said $R^2$ group is optionally substituted by 1 to 5 $R^5$ substituents, each $R^5$ is independently selected from halo, cyano, trifluoromethoxy, trifluoromethyl, —C(O)$R^8$, —$NR^6$C(O)$R^7$, —C(O)$NR^6R^7$, —$NR^6R^7$, —$OR^9$, —$SO_2NR^6R^7$, —$SO_2R^6$, —$NR^6SO_2R^7$, —$NR^6SO_2NR^9R^{10}$, $C_1$–$C_6$ alkyl, $C_2$–$C_6$ alkenyl, $C_2$–$C_6$ alkynyl, —$(CH_2)_jO(CH_2)_qNR^6R^7$, —$(CH_2)_jO(CH_2)_qOR^9$, —$(CH_2)_jOR^9$, —$S(O)_j(C_1$–$C_6$ alkyl), —$(CH_2)_j(C_6$–$C_{10}$ aryl), —$(CH_2)_j(5$ to 10 membered heterocyclic), —$(CH_2)_jO(CH_2)_q(5$ to 10 membered heterocyclic), —$C(O)(CH_2)_j(5$ to 10 membered heterocyclic), —$(CH_2)_jNR^7(CH_2)_qNR^6R^7$, —$(CH_2)_jNR^7CH_2C(O)NR^6R^7$, —$(CH_2)_jNR^7(CH_2)_qNR^9C(O)R^8$, —$(CH_2)_jNR^7(CH_2)_qO(CH_2)_qOR^9$, —$(CH_2)_jNR^7(CH_2)_qS(O)_j(C_1$–$C_6$ alkyl), —$(CH_2)_jNR^7(CH_2)_jR^6$, —$SO_2(CH_2)_t(C_6$–$C_{10}$ aryl), and —$SO_2(CH_2)_t(5$ to 10 membered heterocyclic), wherein j is an integer from 0 to 2, t is an integer from 0 to 6, q is an integer from 2 to 6, the —$(CH_2)_q$— and —$(CH_2)_t$— moieties of the foregoing $R^5$ groups optionally include a carbon-carbon double or triple bond where t is an integer from 2 to 6, and the alkyl, aryl and heterocyclic moieties of the foregoing $R^5$ groups are optionally substituted by 1 to 3 substituents independently selected from halo, cyano, trifluoromethyl, —C(O)$R^8$, —$NR^6C(O)R^7$, —$C(O)NR^6R^7$, —$(CH_2)_tNR^6R^7$, —$SO_2R^6$, —$SO_2NR^6R^7$, $C_1$–$C_6$ alkyl, —$(CH_2)_t(5$ to 10 membered heterocyclic), —(CH$_2$)$_t$O(CH$_2$)$_q$OR$^9$, and —(CH$_2$)$_t$OR$^9$, wherein t is an integer from 0 to 6 and q is an integer from 2 to 6;

each R$^6$ and R$^7$ is independently selected from H, C$_1$–C$_6$ alkyl, —(CH$_2$)$_t$(C$_6$–C$_{10}$ aryl), —(CH$_2$)$_t$(5 to 10 membered heterocyclic), —(CH$_2$)$_t$O(CH$_2$)$_q$OR$^9$, and —(CH$_2$)$_t$OR$^9$, wherein t is an integer from 0 to 6 and q is an integer from 2 to 6, and the alkyl, aryl and heterocyclic moieties of the foregoing R$^6$ and R$^7$ groups are optionally substituted by 1 to 3 substituents independently selected from halo, cyano, trifluoromethyl, —C(O)R$^8$, —NR$^9$C(O)R$^{10}$, —C(O)NR$^9$R$^{10}$, —NR$^9$R$^{10}$, C$_1$–C$_6$ alkyl, —(CH$_2$)$_t$(C$_6$–C$_{10}$ aryl), —(CH$_2$)$_t$(5 to 10 membered heterocyclic), —(CH$_2$)$_t$O (CH$_2$)$_q$OR$^9$, and —(CH$_2$)$_t$OR$^9$, wherein t is an integer from 0 to 6 and q is an integer from 2 to 6, with the proviso that where R$^6$ and R$^7$ are both attached to the same nitrogen, then R$^6$ and R$^7$ are not both bonded to the nitrogen directly through an oxygen;

each R$^8$ is independently selected from H, C$_1$–C$_{10}$ alkyl, —(CH$_2$)$_t$(C$_6$–C$_{10}$ aryl), and —(CH$_2$)$_t$(5 to 10 membered heterocyclic), wherein t is an integer from 0 to 6;

each R$^9$ and R$^{10}$ is independently selected from H and C$_1$–C$_6$ alkyl;

R$^{11}$ is —C(O)NR$^{12}$R$^{13}$, —(CH$_2$)$_t$NR$^{12}$R$^{13}$, —NR$^{12}$C(=O)R$^{13}$, —SO$_2$R$^{12}$, —SO$_2$NR$^{12}$R$^{13}$, —NR$^9$SO$_2$R$^{12}$, —NR$^9$SO$_2$NR$^{12}$R$^{13}$, —C(=N—OR$^{12}$)R$^{13}$, —C(=NR$^{12}$)R$^{13}$, —NR$^9$C(=NR$^{12}$)R$^{13}$, —C(=NR$^{12}$)NR$^9$R$^{13}$, —NR$^9$C(=NR$^{12}$)NR$^9$R$^{13}$, —C(O)R$^{12}$ and —CO$_2$R$^{12}$ and wherein each R$^{12}$ and R$^{13}$ is independently selected from H, C$_1$–C$_6$ alkyl, —(CH$_2$)$_t$(C$_3$–C$_{10}$ cycloalkyl), —(CH$_2$)$_t$(C$_6$–C$_{10}$ aryl), —(CH$_2$)$_t$(5 to 10 membered heterocyclic), —(CH$_2$)$_t$O (CH$_2$)$_q$OR$^9$, —(CH$_2$)$_t$OR$^9$, wherein t is an integer from 0 to 6 and q is an integer from 2 to 6, and the alkyl, aryl and heterocyclic moieties of the foregoing R$^{12}$ and R$^{13}$ groups are optionally substituted by 1 to 3 substituents independently selected from R$^5$ or R$^{12}$ and R$^{13}$ taken together with the nitrogen to which they are attached to form a C$_5$–C$_9$ azabicyclic, aziridinyl, azetidinyl, pyrrolidinyl, piperidinyl, piperazinyl, morpholinyl, thiomorpholinyl, isoquinolinyl, or dihydroisoquinolinyl ring, wherein said C$_5$–C$_9$ azabicyclic, aziridinyl, azetidinyl, pyrrolidinyl, piperidinyl, piperazinyl, morpholinyl, thiomorpholinyl, isoquinolinyl, or dihydroisoquinolinyl ring are optionally substituted by 1 to 5 R$^5$ substituents, with the proviso R$^{12}$ and R$^{13}$ are not both bonded to the nitrogen directly through an oxygen.

More preferred compounds include those of formula 1, wherein X is CH and Y is CH, CF, or N.

Most preferred compounds include those of formula 1, wherein X is CH and Y is N.

Preferred compound include those of formula 1, wherein R$^{11}$ is —C(O)NR$^{12}$R$^{13}$, —SO$_2$R$^{12}$, —SO$_2$NR$^{12}$R$^{13}$, —C(=N—OR$^{12}$)R$^{13}$, and —C(=NR$^{12}$)R$^{13}$.

In one preferred embodiment, the compounds of the invention include those of formula 1 wherein R$^{11}$ is —C(O)NR$^{12}$R$^{13}$, wherein each R$^{12}$ and R$^{13}$ is independently selected from H, C$_1$–C$_6$ alkyl, —(CH$_2$)$_t$OR$^9$, wherein t is an integer from 0 to 6, and the alkyl moiety of the foregoing R$^{12}$ and R$^{13}$ groups is optionally substituted by 1 to 3 substituents independently selected from halo, cyano, trifluoromethyl, —C(O)R$^8$, —NR$^9$C(O)R$^{10}$, —C(O)NR$^9$R$^{10}$, —NR$^9$R$^{10}$, C$_1$–C$_6$ alkyl, —(CH$_2$)$_t$(C$_6$–C$_{10}$ aryl), —(CH$_2$)$_t$(5 to 10 membered heterocyclic), —(CH$_2$)$_t$O (CH$_2$)$_q$OR$^9$, and —(CH$_2$)$_t$OR$^9$, wherein t is an integer from 0 to 6 and q is an integer from 2 to 6, or R$^{12}$ and R$^{13}$ taken together with the nitrogen to which they are attached to form a C$_5$–C$_9$ azabicyclic, aziridinyl, azetidinyl, pyrrolidinyl, piperidinyl, piperazinyl, or morpholinyl ring wherein said C$_5$–C$_9$ azabicyclic, aziridinyl, azetidinyl, pyrrolidinyl, piperidinyl, piperazinyl, or morpholinyl ring are optionally substituted by 1 to 5 R$^5$ substituents, with the proviso R$^{12}$ and R$^{13}$ are not both bonded to the nitrogen directly through an oxygen.

In another preferred embodiment, the compounds of the invention include those of formula 1 wherein R$^{11}$ is —C(O)NR$^{12}$R$^{13}$ wherein R$^{12}$ and R$^{13}$ taken together with the nitrogen to which they are attached form a C$_5$–C$_9$ azabicyclic, aziridinyl, azetidinyl, pyrrolidinyl, piperidinyl, piperazinyl, or morpholinyl ring wherein said C$_5$–C$_9$ azabicyclic, aziridinyl, azetidinyl, pyrrolidinyl, piperidinyl, piperazinyl, or morpholinyl ring are optionally substituted by 1 to 5 R$^5$ substituents.

More preferred compounds of formula 1 include those wherein R$^{11}$ is —C(O)NR$^{12}$R$^{13}$ wherein R$^{12}$ and R$^{13}$ taken together with the nitrogen to which they are attached form a C$_5$–C$_9$ azabicyclic, aziridinyl, azetidinyl, or pyrrolidinyl ring wherein said C$_5$–C$_9$ azabicyclic, aziridinyl, azetidinyl, or pyrrolidinyl ring are optionally substituted by 1 to 5 R$^5$ substituents.

Most preferred compounds of formula 1 include those wherein R$^{11}$ is —C(O)NR$^{12}$R$^{13}$ wherein R$^{12}$ and R$^{13}$ taken together with the nitrogen to which they are attached form a C$_5$–C$_9$ azabicyclic, azetidinyl or pyrrolidinyl ring wherein said C$_5$–C$_9$ azabicyclic, azetidinyl or pyrrolidinyl ring is optionally substituted by 1 to 5 R$^5$ substituents.

Other preferred compounds include those of formula 1 wherein R$^2$ is a group of the formula

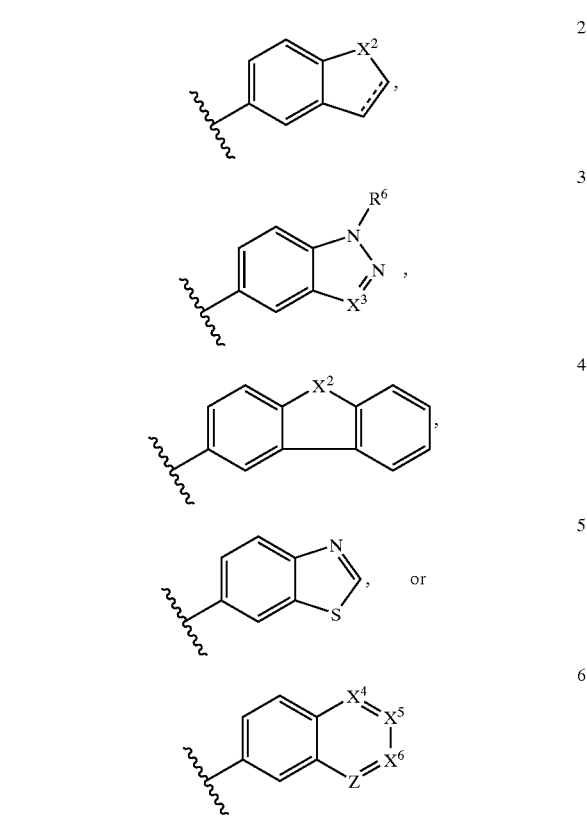

wherein X$^2$ is —S—, —N(R$^6$)— or O, and X$^3$, X$^4$, X$^5$, X$^6$, and Z is N or CH, the dashed line in formula 2 represents an optional double bond, and the above R$^2$ groups of formulas 2, 4 and 6 are optionally substituted by 1 to 5 R$^5$ substituents and the R$^2$ groups of formulas 3 and 5 are optionally substituted by 1 to 3 R$^5$ substituents.

One embodiment of the invention is directed to compounds of formula 1,

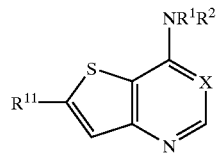

or a pharmaceutically acceptable salt, prodrug or hydrate thereof, wherein X, $R^1$, $R^2$, $R^5$, $R^6$, $R^7$, $R^8$, $R^9$, $R^{10}$, $R^{11}$, $R^{12}$, and $R^{13}$ are as defined above.

One preferred embodiment of the invention is directed to compounds of formula 1, wherein X is CH; Y is N; $R^1$ is H; $R^2$ is

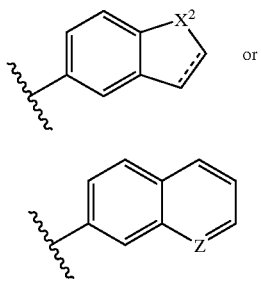

$X^2$ is —N($R^6$)—, the dashed line in formula 2 represents an optional double bond, Z is CH or N and the above $R^2$ group of formulas 2 and 6 are optionally substituted by 1 to 5 $R^5$ and wherein $R^5$, $R^6$, $R^7$, $R^8$, $R^9$, $R^{10}$, $R^{11}$, $R^{12}$, and $R^{13}$ are as defined above.

The invention also relates to compounds of formula 1, wherein X is CH; Y is N; $R^1$ is H; $R^2$ is

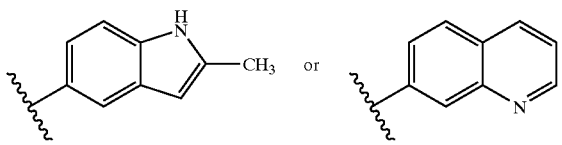

wherein $R^5$, $R^6$, $R^7$, $R^8$, $R^9$, $R^{10}$, $R^{11}$, $R^{12}$, and $R^{13}$ are as defined above.

Specifically preferred compounds include those wherein $R^2$ group is a group of formula 2 or 6, wherein said formulas 2 and 6 are optionally substituted by 1 to 5 $R^5$ substituents.

The following are specific compounds of the present invention:

7-(2-Methyl-1H-indol-5-ylamino)-thieno[3,2-b]pyridine-2-carboxylic acid methyl-pyridin-3-ylmethyl-amide;

Azetidin-1-yl-[7-(2-methyl-1H-indol-5-ylamino)-thieno[3,2-b]pyridin-2-yl]-methanone;

[7-(2-Methyl-1H-indol-5-ylamino)-thieno[3,2-b]pyridin-2-yl]-pyrrolidin-1-yl-methanone;

7-(2-Methyl-1H-indol-5-ylamino)-thieno[3,2-b]pyridine-2-carboxylic acid cyclohexyl-methyl-amide;

(2-Methoxymethyl-pyrrolidin-1-yl)-[7-(2-methyl-1H-indol-5-ylamino)-thieno[3,2-b]pyridin-2-yl]-methanone;

7-(2-Methyl-1H-indol-5-ylamino)-thieno[3,2-b]pyridine-2-carboxylic acid methyl-(2-morpholin-4-yl-ethyl)-amide;

N-{1-[7-(2-Methyl-1H-indol-5-ylamino)-thieno[3,2-b]pyridine-2-carbonyl]-pyrrolidin-3-yl}-acetamide;

N-Ethyl-N-{1-[7-(2-methyl-1H-indol-5-ylamino)-thieno[3,2-b]pyridine-2-carbonyl]-pyrrolidin-3-yl}-acetamide;

(3-Methylamino-pyrrolidin-1-yl)-[7-(2-methyl-1H-indol-5-ylamino)-thieno[3,2-b]pyridin-2-yl]-methanone;

(3-Dimethylamino-pyrrolidin-1-yl)-[7-(2-methyl-1H-indol-5-ylamino)-thieno[3,2-b]pyridin-2-yl]-methanone;

(6-Amino-3-aza-bicyclo[3.1.0]hex-3-yl)-[7-(2-methyl-1H-indol-5-ylamino)-thieno[3,2-b]pyridin-2-yl]-methanone;

(3-Dimethylamino-pyrrolidin-1-yl)-[7-(2-methyl-1H-indol-5-ylamino)-thieno[3,2-b]pyridin-2-yl]-methanone;

(2-Methoxymethyl-pyrrolidin-1-yl)-[7-(2-methyl-1H-indol-5-ylamino)-thieno[3,2-b]pyridin-2-yl]-methanone;

(3-Hydroxy-pyrrolidin-1-yl)-[7-(2-methyl-1H-indol-5-ylamino)-thieno[3,2-b]pyridin-2-yl]-methanone;

(2-Hydroxymethyl-pyrrolidin-1-yl)-[7-(2-methyl-1H-indol-5-ylamino)-thieno[3,2-b]pyridin-2-yl]-methanone;

(3-Methoxy-pyrrolidin-1-yl)-[7-(2-methyl-1H-indol-5-ylamino)-thieno[3,2-b]pyridin-2-yl]-methanone;

(3-Ethoxy-azetidin-1-yl)-[7-(2-methyl-1H-indol-5-ylamino)-thieno[3,2-b]pyridin-2-yl]-methanone;

N-Methyl-N-{1-[7-(2-methyl-1H-indol-5-ylamino)-thieno[3,2-b]pyridine-2-carbonyl]-pyrrolidin-3-yl}-acetamide;

cyclobutanecarboxylic acid {1-[7-(2-methyl-1H-indol-5-ylamino)-thieno[3,2-b]pyridine-2-carbonyl]-pyrrolidin-3-yl}-amide; pharmaceutically acceptable salts of said compounds; solvates of said compounds; and prodrugs of said compounds.

The following are specific preferred compounds of the present invention:

(2S)-(2-Methoxymethyl-pyrrolidin-1-yl)-[7-(2-methyl-1H-indol-5-ylamino)-thieno[3,2-b]pyridin-2-yl]-methanone (+/−)-N-Ethyl-N-{1-[7-(2-methyl-1H-indol-5-ylamino)-thieno[3,2-b]pyridine-2-carbonyl]-pyrrolidin-3-yl}-acetamide (3S)-(3-Dimethylamino-pyrrolidin-1-yl)-[7-(2-methyl-1H-indol-5-ylamino)-thieno[3,2-b]pyridin-2-yl]-methanone (+/−)-N-Methyl-N-{1-[7-(2-methyl-1H-indol-5-ylamino)-thieno[3,2-b]pyridine-2-carbonyl]-pyrrolidin-3-yl}-acetamide (2R)-(2-Methoxymethyl-pyrrolidin-1-yl)-[7-(2-methyl-1H-indol-5-ylamino)-thieno[3,2-b]pyridin-2-yl]-methanone (3S)-(3-Hydroxy-pyrrolidin-1-yl)-[7-(2-methyl-1H-indol-5-ylamino)-thieno[3,2-b]pyridin-2-yl]-methanone (3R)-(3-Hydroxy-pyrrolidin-1-yl)-[7-(2-methyl-1H-indol-5-ylamino)-thieno[3,2-b]pyridin-2-yl]-methanone (+/−)-Cyclobutanecarboxylic acid {1-[7-(2-methyl-1H-indol-5-ylamino)-thieno[3,2-b]pyridine-2-carbonyl]-pyrrolidin-3-yl}-amide 6-Amino-3-aza-bicyclo[3.1.0]hex-3-yl)-[7-(2-methyl-1H-indol-5-ylamino)-thieno[3,2-b]pyridin-2-yl]-methanone (3S)-(3-Methoxy-pyrrolidin-1-yl)-[7-(2-methyl-1H-indol-5-ylamino)-thieno[3,2-b]pyridin-2-yl]-methanone; pharmaceutically acceptable salts of said compounds; solvates of said compounds; and prodrugs of said compounds.

In one embodiment of the invention relates to a method of preparing a compound of the formula 1

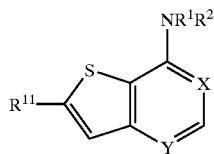

or a pharmaceutically acceptable salt, prodrug or hydrate thereof, which comprises treating a compound of formula 22

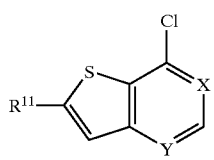

with HNR$^1$R$^2$ wherein X, Y, R$^1$, R$^2$, and R$^{11}$ are as defined above.

In one preferred embodiment of the aforementioned method Y is N.

The invention also relates to a pharmaceutical composition for the treatment of pancreatitis or kidney disease (including proliferative glomerulonephritis and diabetes-induced renal disease) in a mammal which comprises a therapeutically effective amount of a compound of formula 1, or a pharmaceutically acceptable salt, prodrug or hydrate thereof, and a pharmaceutically acceptable carrier.

The invention also relates to a pharmaceutical composition for the prevention of blastocyte implantation in a mammal which comprises a therapeutically effective amount of a compound of formula 1, or a pharmaceutically acceptable salt, prodrug or hydrate thereof, and a pharmaceutically acceptable carrier.

The invention also relates to a pharmaceutical composition for treating a disease related to vasculogenesis or angiogenesis in a mammal which comprises a therapeutically effective amount of a compound of formula 1, or a pharmaceutically acceptable salt, prodrug or hydrate thereof, and a pharmaceutically acceptable carrier. In one embodiment, said pharmaceutical composition is for treating a disease selected from the group consisting of tumor angiogenesis, chronic inflammatory disease such as rheumatoid arthritis, atherosclerosis, skin diseases such as psoriasis, excema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

The invention also relates to a method of treating a hyperproliferative disorder in a mammal which comprises administering to said mammal a therapeutically effective amount of the compound of formula 1, or a pharmaceutically acceptable salt, prodrug or hydrate thereof. In one embodiment, said method relates to the treatment of cancer such as brain, squamous cell, bladder, gastric, pancreatic, breast, head, neck, oesophageal, prostate, colorectal, lung, renal, kidney, ovarian, gynecological or thyroid cancer. In another embodiment, said method relates to the treatment of a non-cancerous hyperproliferative disorder such as benign hyperplasia of the skin (e.g., psoriasis) or prostate (e.g., benign prostatic hypertropy (BPH)).

The invention also relates to a method for the treatment of a hyperproliferative disorder in a mammal which comprises administering to said mammal a therapeutically effective amount of a compound of formula 1, or a pharmaceutically acceptable salt, prodrug or hydrate thereof, in combination with an anti-tumor agent selected from the group consisting of, but not limited to, mitotic inhibitors, alkylating agents, anti-metabolites, intercalating agents, growth factor inhibitors, cell cycle inhibitors, enzymes, topoisomerase inhibitors, biological response modifiers, anti-hormones, kinase inhibitors, matrix metalloprotease inhibitors, genetic therapeutics and anti-androgens.

The invention also relates to a method of treating pancreatitis or kidney disease in a mammal which comprises administering to said mammal a therapeutically effective amount of a compound of formula 1, or a pharmaceutically acceptable salt, prodrug or hydrate thereof.

The invention also relates to a method of preventing blastocyte implantation in a mammal which comprises administering to said mammal a therapeutically effective amount of a compound of formula 1, or a pharmaceutically acceptable salt, prodrug or hydrate thereof.

The invention also relates to a method of treating diseases related to vasculogenesis or angiogenesis in a mammal which comprises administering to said mammal an effective amount of a compound of formula 1, or a pharmaceutically acceptable salt, prodrug or hydrate thereof. In one embodiment, said method is for treating a disease selected from the group consisting of tumor angiogenesis, chronic inflammatory disease such as rheumatoid arthritis, atherosclerosis, skin diseases such as psoriasis, excema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

Patients that can be treated with a compounds of formula 1, and the pharmaceutically acceptable salts, prodrugs and hydrates of said compounds, according to the methods of this invention include, for example, patients that have been diagnosed as having psoriasis, BPH, lung cancer, bone cancer, pancreatic cancer, skin cancer, cancer of the head and neck, cutaneous or intraocular melanoma, uterine cancer, ovarian cancer, rectal cancer, cancer of the anal region, stomach cancer, colon cancer, breast cancer, gynecologic tumors (e.g., uterine sarcomas, carcinoma of the fallopian tubes, carcinoma of the endometrium, carcinoma of the cervix, carcinoma of the vagina or carcinoma of the vulva), Hodgkin's disease, cancer of the esophagus, cancer of the small intestine, cancer of the endocrine system (e.g., cancer of the thyroid, parathyroid or adrenal glands), sarcomas of soft tissues, cancer of the urethra, cancer of the penis, prostate cancer, chronic or acute leukemia, solid tumors of childhood, lymphocytic lymphonas, cancer of the bladder, cancer of the kidney or ureter (e.g., renal cell carcinoma, carcinoma of the renal pelvis), or neoplasms of the central nervous system (e.g., primary CNS lymphona, spinal axis tumors, brain stem gliomas or pituitary adenomas).

This invention also relates to a pharmaceutical composition for inhibiting abnormal cell growth in a mammal which comprises an amount of a compound of formula 1, or a pharmaceutically acceptable salt or solvate or prodrug thereof, in combination with an amount of a chemotherapeutic, wherein the amounts of the compound, salt, solvate, or prodrug, and of the chemotherapeutic are together effective in inhibiting abnormal cell growth. Many chemotherapeutics are presently known in the art. In one embodiment, the chemotherapeutic is selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, e.g. anti-androgens.

This invention further relates to a method for inhibiting abnormal cell growth in a mammal which method comprises administering to the mammal an amount of a compound of formula 1, or a pharmaceutically acceptable salt or solvate or prodrug thereof, in combination with radiation therapy, wherein the amount of the compound, salt, solvate or prodrug is in combination with the radiation therapy effective in inhibiting abnormal cell growth in the mammal. Techniques for administering radiation therapy are known in the art, and these techniques can be used in the combination therapy described herein. The administration of the compound of the invention in this combination therapy can be determined as described herein.

It is believed that the compounds of formula 1 can render abnormal cells more sensitive to treatment with radiation for purposes of killing and/or inhibiting the growth of such cells. Accordingly, this invention further relates to a method for sensitizing abnormal cells in a mammal to treatment with radiation which comprises administering to the mammal an amount of a compound of formula 1 or pharmaceutically acceptable salt, prodrug or solvate thereof, which amount is effective in sensitizing abnormal cells to treatment with radiation. The amount of the compound, salt, or solvate in this method can be determined according to the means for ascertaining effective amounts of such compounds described herein.

This invention also relates to a pharmaceutical composition for inhibiting abnormal cell growth in a mammal, including a human, comprising an amount of a compound of the formula 1 as defined above, or a pharmaceutically acceptable salt, prodrug or solvate thereof, that is effective in inhibiting farnesyl protein transferase, and a pharmaceutically acceptable carrier.

This invention further relates to a pharmaceutical composition for inhibiting abnormal cell growth in a mammal comprising an amount of a compound of formula 1, or a pharmaceutically acceptable salt or solvate or prodrug thereof, that is effective in inhibiting abnormal cell growth, and a pharmaceutically acceptable carrier.

This invention also relates to a method of and to a pharmaceutical composition for inhibiting abnormal cell growth in a mammal which comprises an amount of a compound of formula 1, a pharmaceutically acceptable salt or solvate thereof, a prodrug thereof, or an isotopically-labelled derivative thereof, and an amount of one or more substances selected from anti-angiogenesis agents, signal transduction inhibitors, and antiproliferative agents.

This invention also relates to a pharmaceutical composition for inhibiting abnormal cell growth in a mammal, including a human, comprising an amount of a compound of formula 1 as defined above, or a pharmaceutically acceptable salt or solvate thereof, that is effective in inhibiting farnesyl protein transferase, and a pharmaceutically acceptable carrier.

This invention also relates to a method of and to a pharmaceutical composition for inhibiting abnormal cell growth in a mammal which comprises an amount of a compound of formula 1, a pharmaceutically acceptable salt or solvate thereof, a prodrug thereof, or an isotopically-labelled derivative thereof, and an amount of one or more substances selected from anti-angiogenesis agents, signal transduction inhibitors, and antiproliferative agents.

Anti-angiogenesis agents, such as MMP-2 (matrix-metalloprotienase 2) inhibitors, MMP-9 (matrix-metalloprotienase 9) inhibitors, and COX-II (cyclooxygenase II) inhibitors, can be used in conjunction with a compound of formula 1 and pharmaceutical compositions described herein. Examples of useful COX-II inhibitors include CELEBREX™ (alecoxib), valdecoxib, and rofecoxib. Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931,788 (published Jul. 28, 1999), WO 90/05719 (published May 331, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25,1999), Great Britain patent application number 9912961.1 (filed Jun. 3, 1999), U.S. Provisional Application No. 60/148,464 (filed Aug. 12, 1999), U.S. Pat. No. 5,863,949 (issued Jan. 26, 1999), U.S. Pat. No. 5,861,510 (issued Jan. 19, 1999), and European Patent Publication 780,386 (published Jun. 25, 1997), all of which are incorporated herein in their entireties by reference. Preferred MMP inhibitors are those that do not demonstrate arthralgia. More preferred, are those that selectively inhibit MMP-2 and/or MMP-9 relative to the other matrix-metalloproteinases (i.e. MMP-1, MMP-3, MMP-4, MMP-5, MMP-6, MMP-7, MMP-8, MMP-10, MMP-11, MMP-12, and MMP-13).

Some specific examples of MMP inhibitors useful in the present invention are AG-3340, RO 32-3555, RS 13-0830, and the compounds recited in the following list:

3-[[4-(4-fluoro-phenoxy)-benzenesulfonyl]-(1-hydroxycarbamoyl-cyclopentyl)-amino]-propionic acid;

3-exo-3-[4-(4-fluoro-phenoxy)-benzenesulfonylamino]-8-oxa-bicyclo[3.2.1]octane-3-carboxylic acid hydroxyamide;

(2R, 3R) 1-[4-(2-chloro-4-fluoro-benzyloxy)-benzenesulfonyl]-3-hydroxy-3-methyl-piperidine-2-carboxylic acid hydroxyamide;

4-[4-(4-fluoro-phenoxy)-benzenesulfonylamino]-tetrahydro-pyran-4-carboxylic acid hydroxyamide;

3-[[4-(4-fluoro-phenoxy)-benzenesulfonyl]-(1-hydroxycarbamoyl-cyclobutyl)-amino]-propionic acid;

4-[4-(4-chloro-phenoxy)-benzenesulfonylamino]-tetrahydro-pyran-4-carboxylic acid hydroxyamide;

(R) 3-[4-(4-chloro-phenoxy)-benzenesulfonylamino]-tetrahydro-pyran-3-carboxylic acid hydroxyamide;

(2R, 3R) 1-[4-(4-fluoro-2-methyl-benzyloxy)-benzenesulfonyl]-3-hydroxy-3-methyl-piperidine-2-carboxylic acid hydroxyamide;

3-[[4-(4-fluoro-phenoxy)-benzenesulfonyl]-(1-hydroxycarbamoyl-1-methyl-ethyl)-amino]-propionic acid;

3-[[4-(4-fluoro-phenoxy)-benzenesulfonyl]-(4-hydroxycarbamoyl-tetrahydro-pyran-4-yl)-amino]-propionic acid;

3-exo-3-[4-(4-chloro-phenoxy)-benzenesulfonylamino]-8-oxa-bicyclo[3.2.1]octane-3-carboxylic acid hydroxyamide;

3-endo-3-[4-(4-fluoro-phenoxy)-benzenesulfonylamino]-8-oxa-bicyclo[3.2.1]octane-3-carboxylic acid hydroxyamide; and (R) 3-[4-(4-fluoro-phenoxy)-benzenesulfonylamino]-tetrahydro-furan-3-carboxylic acid hydroxyamide;

and pharmaceutically acceptable salts and solvates of said compounds.

A compound of formula 1 can also be used with signal transduction inhibitors, such as agents that can inhibit EGFR (epidermal growth factor receptor) responses, such as EGFR antibodies, EGF antibodies, and molecules that are EGFR inhibitors; VEGF (vascular endothelial growth factor) inhibitors, such as VEGF receptors and molecules that can inhibit VEGF; and erbB2 receptor inhibitors, such as organic molecules or antibodies that bind to the erbB2 receptor, for example, HERCEPTIN™ (Genentech, Inc. of South San Francisco, Calif., USA).

EGFR inhibitors are described in, for example in WO 95/19970 (published Jul. 27, 1995), WO 98/14451 (published Apr. 9, 1998), WO 98/02434 (published Jan. 22, 1998), and U.S. Pat. No. 5,747,498 (issued May 5, 1998), and such substances can be used in the present invention as described herein. EGFR-inhibiting agents include, but are not limited to, the monoclonal antibodies C225 and anti-EGFR 22Mab (ImClone Systems Incorporated of New York, N.Y., USA), ABX-EGF (Abgenix/Cell Genesys), EMD-7200 (Merck KgaA), EMD-5590 (Merck KgaA), MDX-447/H-477 (Medarex Inc. of Annandale, N.J., USA and Merck KgaA), and the compounds ZD-1834, ZD-1838 and ZD-1839 (AstraZeneca), PKI-166 (Novartis), PKI-166/CGP-75166 (Novartis), PTK 787 (Novartis), CP 701 (Cephalon), leflunomide (Pharmacia/Sugen), CI-1033 (Warner Lambert Parke Davis), CI-1033/PD 183,805 (Warner Lambert Parke Davis), CL-387,785 (Wyeth-Ayerst), BBR-1611 (Boehringer Mannheim GmbH/Roche), Naamidine A (Bristol Myers Squibb), RC-3940-II (Pharmacia), BIBX-1382 (Boehringer Ingelheim), OLX-103 (Merck & Co. of Whitehouse Station, N.J., USA), VRCTC-310 (Ventech Research), EGF fusion toxin (Seragen Inc. of Hopkinton, Mass.), DAB-389 (Seragen/Lilgand), ZM-252808 (Imperical Cancer Research Fund), RG-50864 (INSERM), LFM-A12 (Parker Hughes Cancer Center), WHI-P97 (Parker Hughes Cancer Center), GW-282974 (Glaxo), KT-8391 (Kyowa Hakko) and EGFR Vaccine (York Medical/Centro de Immunologia Molecular (CIM)). These and other EGFR-inhibiting agents can be used in the present invention.

VEGF inhibitors, for example SU-5416 and SU-6668 (Sugen Inc. of South San Francisco, Calif., USA), SH-268 (Schering), and NX-1838 (NeXstar) can also be combined with the compound of the present invention. VEGF inhibitors are described in, for example in WO 99/24440 (published May 20, 1999), PCT International Application PCT/IB99/00797 (filed May 3, 1999), in WO 95/21613 (published Aug. 17, 1995), WO 99/61422 (published Dec. 2, 1999), U.S. Pat. No. 5,834,504 (issued Nov. 10, 1998), WO 98/50356 (published Nov. 12, 1998), U.S. Pat. No. 5,883,113 (issued Mar. 16, 1999), U.S. Pat. No. 5,886,020 (issued Mar. 23, 1999), U.S. Pat. No. 5,792,783 (issued Aug. 11, 1998), WO 99/10349 (published Mar. 4, 1999), WO 97/32856 (published Sep. 12, 1997), WO 97/22596 (published Jun. 26, 1997), WO 98/54093 (published Dec. 3, 1998), WO 98/02438 (published Jan. 22, 1998), WO 99/16755 (published Apr. 8, 1999), and WO 98/02437 (published Jan. 22, 1998), all of which are incorporated herein in their entireties by reference. Other examples of some specific VEGF inhibitors useful in the present invention are IM862 (Cytran Inc. of Kirkland, Wash., USA); anti-VEGF monoclonal antibody of Genentech, Inc. of South San Francisco, Calif.; and angiozyme, a synthetic ribozyme from Ribozyme (Boulder, Colo.) and Chiron (Emeryville, Calif.). These and other VEGF inhibitors can be used in the present invention as described herein.

ErbB2 receptor inhibitors, such as GW-282974 (Glaxo Wellcome plc), and the monoclonal antibodies AR-209 (Aronex Pharmaceuticals Inc. of The Woodlands, Tex., USA) and 2B-1 (Chiron), can furthermore be combined with the compound of the invention, for example those indicated in WO 98/02434 (published Jan. 22, 1998), WO 99/35146 (published Jul. 15, 1999), WO 99/35132 (published Jul. 15, 1999), WO 98/02437 (published Jan. 22, 1998), WO 97/13760 (published Apr. 17, 1997), WO 95/19970 (published Jul. 27, 1995), U.S. Pat. No. 5,587,458 (issued Dec. 24, 1996), and U.S. Pat. No. 5,877,305 (issued Mar. 2, 1999), which are all hereby incorporated herein in their entireties by reference. ErbB2 receptor inhibitors useful in the present invention are also described in U.S. Provisional Application No. 60/117,341, filed Jan. 27, 1999, and in U.S. Provisional Application No. 60/117,346, filed Jan. 27, 1999, both of which are incorporated in their entireties herein by reference. The erbB2 receptor inhibitor compounds and substance described in the aforementioned PCT applications, U.S. patents, and U.S. provisional applications, as well as other compounds and substances that inhibit the erbB2 receptor, can be used with the compound of the present invention in accordance with the present invention.

The compound of the invention can also be used with other agents useful in treating abnormal cell growth or cancer, including, but not limited to, agents capable of enhancing antitumor immune responses, such as CTLA4 (cytotoxic lymphocite antigen 4) antibodies, and other agents capable of blocking CTLA4; and anti-proliferative agents such as other farnesyl protein transferase inhibitors, and the like. Specific CTLA4 antibodies that can be used in the present invention include those described in U.S. Provisional Application No. 60/113,647 (filed Dec. 23, 1998) which is incorporated by reference in its entirety, however other CTLA4 antibodies can be used in the present invention.

Other anti-angiogenesis agents, including, but not limited to, other COX-II inhibitors, other MMP inhibitors, other anti-VEGF antibodies or inhibitors of other effectors of vascularization can also be used in the present invention.

The subject invention also includes isotopically-labelled compounds, which are identical to those recited in formula 1 but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^{3}H$ and $^{14}C$ are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labelled compounds of formula 1 of this invention and prodrugs thereof can generally be prepared by carrying out the procedures disclosed in the Schemes and/or in the Examples below, by substituting a readily available isotopically labelled reagent for a non-isotopically labelled reagent.

The compounds of formula 1 and their pharmaceutically acceptable salts and solvates can each independently also furthermore be used in a palliative neo-adjuvant/adjuvant therapy in alleviating the symptoms associated with the diseases recited herein as well as the symptoms associated with abnormal cell growth. Such therapy can be a monotherapy or can be in a combination with chemotherapy and/or immunotherapy.

The terms "abnormal cell growth" and "hyperproliferative disorder" are used interchangeably in this application.

"Abnormal cell growth", as used herein, refers to cell growth that is independent of normal regulatory mechanisms (e.g., loss of contact inhibition), including the abnormal growth of normal cells and the growth of abnormal cells. This includes, but is not limited to, the abnormal growth of: (1) tumor cells (tumors), both benign and malignant, expressing an activated Ras oncogene; (2) tumor cells, both benign and malignant, in which the Ras protein is activated as a result of oncogenic mutation in another gene; (3) benign and malignant cells of other proliferative diseases in which aberrant Ras activation occurs. Examples of such benign proliferative diseases are psoriasis, benign prostatic hypertrophy, human papilloma virus (HPV), and restinosis. "Abnormal cell growth" also refers to and includes the abnormal growth of cells, both benign and malignant, resulting from activity of the enzyme farnesyl protein transferase.

The term "treating", as used herein, unless otherwise indicated, means reversing, alleviating, inhibiting the progress of, or preventing the disorder or condition to which such term applies, or one or more symptoms of such disorder or condition. The term "treatment", as used herein, refers to the act of treating, as "treating" is defined immediately above.

The term "halo", as used herein, unless otherwise indicated, means fluoro, chloro, bromo or iodo. Preferred halo groups are fluoro, chloro and bromo.

The term "alkyl", as used herein, unless otherwise indicated, means saturated monovalent hydrocarbon radicals having straight, cyclic or branched moieties. Said "alkyl" group may include an optional carbon-carbon double or triple bond where said alkyl group comprises at least two carbon atoms. It is understood that for cyclic moieties at least three carbon atoms are required in said alkyl group.

The term "alkenyl", as used herein, unless otherwise indicated, means straight or branched chain alkyl moieties having at least one carbon-carbon double bond. Examples, without limitation, of alkenyl groups include 1-propenyl, 1- and 2-butenyl, etc.

The term "alkynyl", as used herein, unless otherwise indicated, means straight or branched chain alkyl moieties having at least one carbon-carbon triple bond. Examples, without limitation, of alkynyl groups include 1-propynyl, 1- and 2-butynyl, etc.

The term "alkoxy", as used herein, unless otherwise indicated, means O-alkyl groups wherein "alkyl" is as defined above.

The term "aryl", as used herein, unless otherwise indicated, means an organic radical derived from an aromatic hydrocarbon by removal of one hydrogen, such as phenyl or naphthyl.

The term "cycloalkyl", as used herein, unless otherwise indicated, means an all-carbon monocyclic ring. Examples, without limitation, of cycloalkyl groups are cyclopropyl, cyclobutyl, cyclopentyl, and cyclohexyl.

The term "5 to 10 membered heterocyclic" or "5 to 13 membered heterocyclic", as used herein, unless otherwise indicated, means aromatic and non-aromatic heterocyclic groups containing one to four heteroatoms each selected from O, S and N, wherein each heterocyclic group has from 5 to 10 or 5 to 13 atoms in its ring system. The heterocyclic groups include benzo-fused ring systems and ring systems substituted with one or two oxo (=O) moieties such as pyrrolidin-2-one. An example of a 5 membered heterocyclic group is thiazolyl, an example of a 10 membered heterocyclic group is quinolinyl and an example of a 13 membered heterocyclic group is a carbazole group. Examples of non-aromatic heterocyclic groups are pyrrolidinyl, tetrahydrofuranyl, tetrahydrothienyl, tetrahydropyranyl, tetrahydrothiopyranyl, piperidino, morpholino, thiomorpholino, thioxanyl, piperazinyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo [3.1.0]hexanyl, 3-azabicyclo[4.1.0]heptanyl, 3H-indolyl and quinolizinyl. Examples of aromatic heterocyclic groups are imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, benzo[1,3]dioxolyl, quinazolinyl, quinoxalinyl, naphthyridinyl, and furopyridinyl. The foregoing groups, as derived from the compounds listed above, may be C-attached or N-attached where such is possible. For instance, a group derived from pyrrole may be pyrrol-1-yl (N-attached) or pyrrol-3-yl (C-attached).

The phrase "pharmaceutically acceptable salt(s)", as used herein, unless otherwise indicated, includes salts of acidic or basic groups which may be present in the compounds of formula 1. The compounds of formula 1 that are basic in nature are capable of forming a wide variety of salts with various inorganic and organic acids. The acids that may be used to prepare pharmaceutically acceptable acid addition salts of such basic compounds of formula 1 are those that form non-toxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate [i.e., 1,1'-methylene-bis-(2-hydroxy-3-naphthoate)] salts.

Those compounds of the formula 1 that are acidic in nature, are capable of forming base salts with various pharmacologically acceptable cations. Examples of such salts include the alkali metal or alkaline earth metal salts and particularly, the sodium and potassium salts.

The compounds of the present invention have asymmetric centers and therefore exist in different enantiomeric and diastereomeric forms. This invention relates to the use of all optical isomers and stereoisomers of the compounds of the present invention, and mixtures thereof, and to all pharmaceutical compositions and methods of treatment that may employ or contain them. The compounds of formula 1 may also exist as tautomers. This invention relates to the use of all such tautomers and mixtures thereof.

This invention also encompasses pharmaceutical compositions containing and methods of treating proliferative disorders or abnormal cell growth through administering prodrugs of compounds of the formula 1. Compounds of formula 1 having free amino, amido, hydroxy or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of formula 1. The amino acid residues include but are not limited to the 20 naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone. Additional types of prodrugs are also encompassed. For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxycarbonyls, as outlined in *Advanced Drug Delivery Reviews*, 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in *J. Med. Chem.* 1996, 39, 10. Free amines can also be derivatized as amides, sulfonamides or phosphonamides. All of these prodrug moieties may incorporate groups including but not limited to ether, amine and carboxylic acid functionalities.

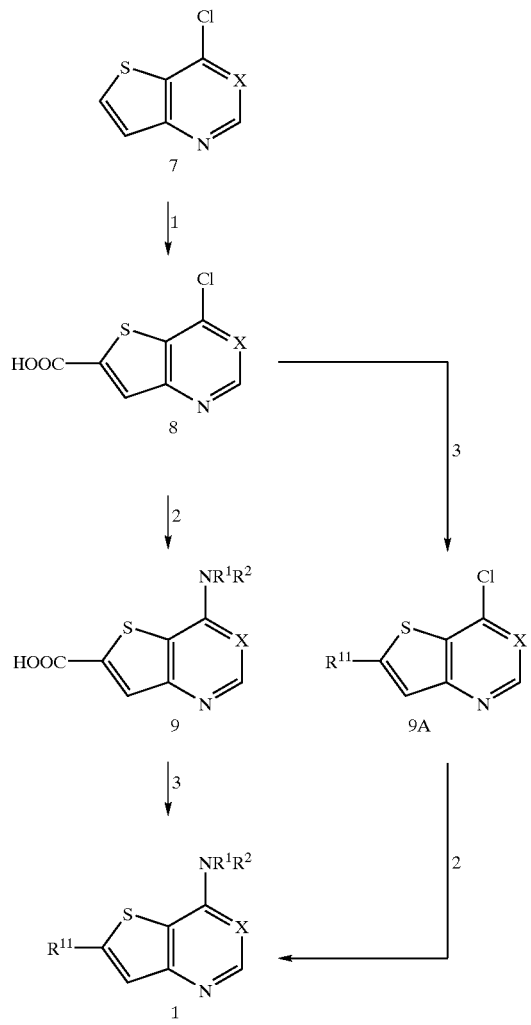

Scheme 1

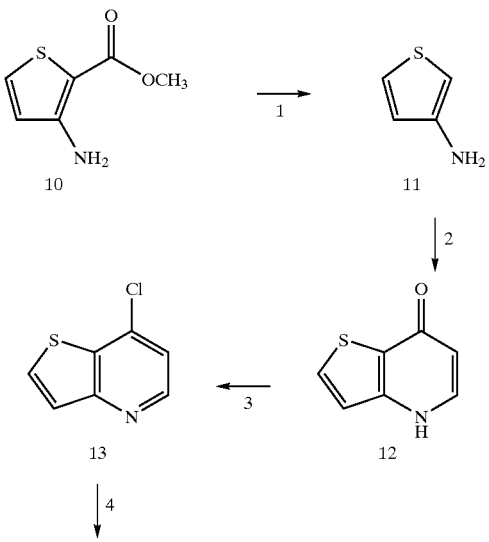

Scheme 2

17

-continued

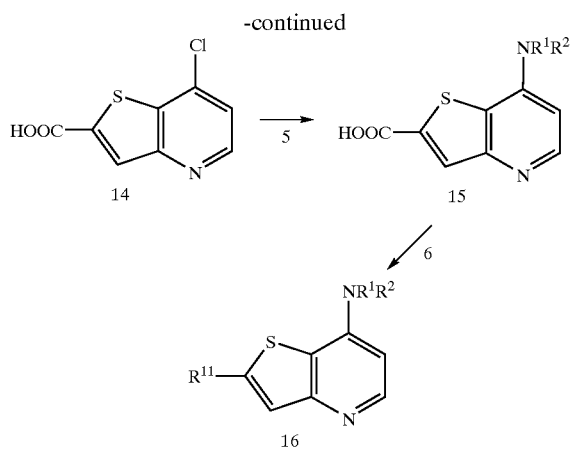

Scheme 3

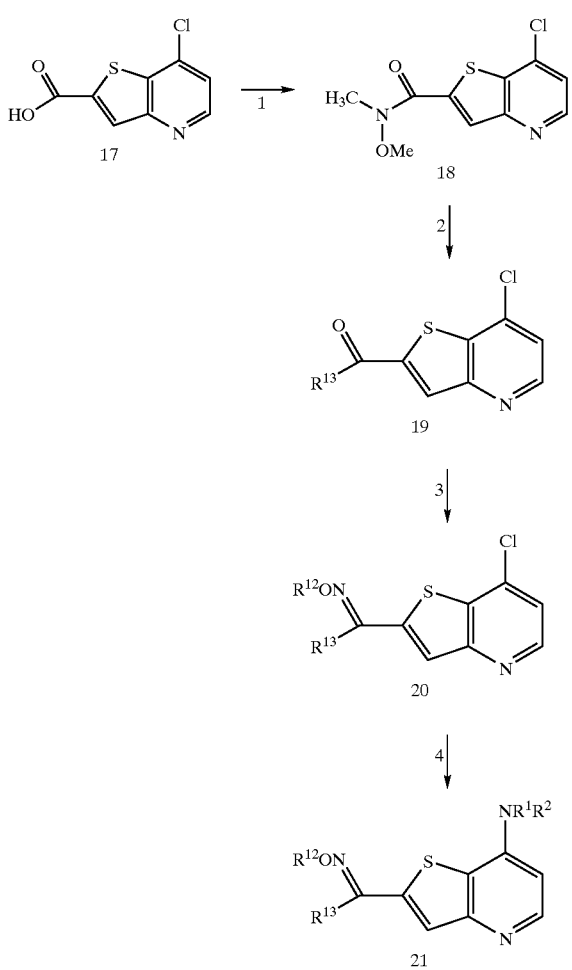

DETAILED DESCRIPTION OF THE INVENTION

The preparation of the compounds of the present invention is illustrated in Schemes 1–3.

The compounds of the present invention are readily prepared according to synthetic methods familiar to those skilled in the art. Scheme 1 illustrates a general synthetic procedure for preparing the compounds of the present invention. The compound of formula (in which X is as defined above) may be prepared by one or more procedures described in published PCT international applications numbers WO 95/19774 (published Jul. 27, 1995), WO 95/19970 (published Jul. 27, 1995), and WO 97/13771 (published Apr. 17, 1997). In addition, 4-chlorothieno[3,2-d]pyrimidine is commercially available, such as from Maybridge Chemical Co. Ltd. A preferred method of preparing 4-chlorothieno[3,2-d]pyridine is described below with reference to steps 1–3 of Scheme 2.

In step 1 of Scheme 1, the compound of formula 7 may be converted to the corresponding carboxy derivative of formula 8 by treating the starting compound, for example, with lithium diisopropylamine or n-butyllithium, and then carbon dioxide gas in a non-polar solvent, such as tetrahydrofuran (THF), at a temperature of about −78° C. for a period of about 15 minutes to one-half hour and then gradually warming the mixture to room temperature (20–25° C.).

In step 2 of Scheme 1, the compound of formula 8 may be coupled with a compound of formula $HNR^1R^2$, wherein $R^1$ and $R^2$ are as defined above, optionally in the presence of a base, such as pyridine, triethylamine or sodium hydride, and optionally in the presence of pyridine hydrochloride as a catalyst, under an inert atmosphere, such as dry nitrogen gas, in a solvent, such as a $C_1$–$C_6$ alcohol, dimethylformamide (DMF), 1,2-dichloroethane (DCE), N-methylpyrrolidin-2-one (NMP), chloroform, acetonitrile, tetrahydrofuran (THF), dimethylsulfoxide (DMSO), 1,4-dioxane or pyridine, or a mixture of two or more of the foregoing solvents, preferably a mixture of t-butyl alcohol and DCE, at a temperature of from ambient to reflux temperature, preferably 80–125° C., for a period of about 2 hours to 72 hours to provide the compound of formula 9.

Where the compound of formula $HNR^1R^2$ is an optionally substituted indole or indoline moiety, such compounds can be prepared according to one or more methods known to those skilled in the art. Such methods are described in PCT international patent application publication number WO 95/23141, referred to above, and in W. C. Sumpter and F. M. Miller, "Heterocyclic Compounds with Indole and Carbazole Systems," in volume 8 of "The Chemistry of Heterocyclic Compounds", Interscience Publishers Inc., New York (1954). Where the compound of formula $HNR^1R^2$ is an optionally substituted quinoline, isoquinoline, or quinazoline derivative, such compounds can also be prepared according to one or more methods known to those skilled in the art. Such methods are described in A. R. Katrizky, C. W. Rees, and E. F. V. Scriven, "Comprehensive Heterocyclic Chemistry II", volumes 5, 6, and 7, Elsevier Science Ltd., Oxford (1996). Optional substituents can be included as appropriate before or after the coupling step illustrated in Scheme 1. Prior to the coupling step, primary and secondary amino moieties (other than said amine of formula $HNR^1R^2$) are preferably protected using a nitrogen protecting group known to those skilled in the art. Such protecting groups and their use are described in T. W. Greene and P. G. M. Wuts, "Protective Groups in Organic Synthesis," Second Edition, John Wiley & Sons, New York, 1991.

In step 3 of Scheme 1, transformation of the carboxy derivative of formula 8 to the compound of formula 9 is carried out using standard synthetic methods well known to those of ordinary skill in the art, such as described in B. S. Furniss, A. J. Hannaford, P. W. G. Smith and A. R. Tatchell, "Vogel's Textbook of Practical Organic Chemistry," Fifth Edition, Longman, Harlow, England, 1996. Optional substitutents on the $R^{11}$ group can be included as appropriate using methods well known to those of ordinary skill in the art, before or after step 3 of Scheme 1.

In the alternative, steps 2 and 3 of Scheme 1 may be reversed. That is, the $R^{11}$ group may be introduced into the compound of formula 8 to form compound of formula 9A prior to the addition of $HNR^1R^2$ to form compound of formula 1 as described above.

Scheme 2 illustrates a procedure for preparing the compounds of formula 1 wherein X is CH. In step 1 of Scheme 2, the compound of formula 10 (3-amino-thiophene-2-carboxylic acid methyl ester) is dissolved in sodium hydroxide and refluxed for about 2 hours. The solution is then cooled to 0° C. and acidified to pH 5 with concentrated HCl at which time a precipitate will form. The precipitate is separated and treated with propanol and oxalic acid, and the solution is stirred at about 38° C. for approximately 45 minutes to provide the compound of formula 11 (thiophen-3-ylamine). In step 2 of Scheme 2, the compound of formula 11 is dissolved in triethyl orthoformate and stirred at room temperature until dissolution is complete. 2,2-Dimethyl-[1,3]dioxane-4,6-dione is then added portionwise at room temperature, with a precipitate forming upon completion of the addition. The mixture is then heated at 85° C. overnight. The resulting precipitate, which is an intermediate (2,2-dimethyl-5-(thiophen-3-ylaminomethylene)-[1,3]dioxane-4,6-dione), is then separated and washed. The intermediate is added to dowtherm A (heated to 260° C.), and the resulting mixture is heated for 30 minutes and then cooled to room temperature to provide the compound of formula 12. In step 3 of Scheme 2, the compound of formula 12 is added to oxalyl chloride in a mixture of methylene chloride and DMF and heated to reflux for approximately two hours to provide the compound of formula 13. The compound of formula 13 may be converted to the compound of formula 14 as described above with respect to step 1 of Scheme 1. The compound of formula 14 may be converted to the compound of formula 15 as described above with respect to step 2 of Scheme 1. The compound of formula 15 may be converted to the compound of formula 16 as described above with respect to step 3 of Scheme 1.

Scheme 3 illustrates a procedure for preparing the compounds of formula 1 wherein X is CH, Y is N and $R^{11}$ is a ketone or oxime derivative. In step 1 of Scheme 3, the compound of formula 17 is treated with $SOCl_2$ in an inert solvent such as dichloromethane and refluxed for about 2 hours. Subsequent treatment with dimethylhydroxylamine affords a compound of formula 18. Treatment of compound 18 with an organometallic derivative of the form $R^{13}M$, where M is a metal ion such as magnesium or lithium, affords ketones of the formula 19. Addition of amino groups of the form $HNR^1R^2$ can be carried out at this point by a procedure analogous to step 2 of scheme 1. Alternatively, condensation of compounds of the formula 19 with amine derivatives of the form $R^{12}ONH_2$ can be carried out under dehydrating conditions to give oxime derivatives of the formula 20. Step 4 of Scheme 3 is carried out as described for step 2 of Scheme 1 to provide compounds of formula 21.

In order to make a compound of formula 1 wherein $R^{11}$ is $C(O)NR^{12}R^{13}$, the compound of fomula 9 is coupled, for example, with $HNR^{12}R^{13}$ using coupling methods well known to those of ordinary skill in the art. See, PCT international application number WO 94/07910, which is incorporated herein by reference in its entirety. Alternatively, the compound of formula 8 can be transformed into the acid chloride derivative by treating it with oxalyl or thionyl chloride in dichloromethane at room temperature for 2–4 hours. The resulting acid chloride is then treated with a compound of formula $HNR^{12}R^{13}$ to provide the desired compound of formula 1 wherein $R^{11}$ is an amide derivative.

A compound of formula 1 wherein $R^{11}$ is a sulfonyl derivative can be prepared by treating a compound of formula 7, as described in step 1 of Scheme 1, with sulfonyl or sulfonamidyl halide in place of carbon dioxide.

When the $R^{11}$ subsituent of formula 1 is linked through an amino group, transformation of the carboxy group of compound 8 to the amino group is first required. This can be accomplished using the Curtius reaction, wherein the acid chloride derivative of compound 8 is treated with, for example, sodium azide, and the resulting acyl azide is allowed to decompose in the presence of acid to afford the amino derivative. The resulting amino compound can be further functionalized by acylating with a variety of carboxylic acids, acid chlorides, sulfonic acids, acid chlorides, or guanylating agents to produce a variety of $R^{11}$ groups, such as, $-NR^{12}C(=O)R^{13}$, $-NR^9SO_2R^{12}$, $-NR^9SO_2NR^{12}R^{13}$, $-NR^9C(=NR^{12})R^{13}$, and $-NR^9C(=NR^{12})NR^9R^{13}$.

The compounds of the present invention may have asymmetric carbon atoms. Such diasteromeric mixtures can be separated into their individual diastereomers on the basis of their physical chemical differences by methods known to those skilled in the art, for example, by chromatography or fractional crystallization. Enantiomers can be separated by converting the enantiomeric mixtures into a diastereomric mixture by reaction with an appropriate optically active compound (e.g., alcohol), separating the diastereomers and converting (e.g., hydrolyzing) the individual diastereomers to the corresponding pure enantiomers. All such isomers, including diastereomer mixtures and pure enantiomers are considered as part of the invention.

The compounds of formula 1 that are basic in nature are capable of forming a wide variety of different salts with various inorganic and organic acids. Although such salts must be pharmaceutically acceptable for administration to animals, it is often desirable in practice to initially isolate the compound of formula 1 from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The desired acid salt can also be precipitated from a solution of the free base in an organic solvent by adding to the solution an appropriate mineral or organic acid.

Those compounds of formula 1 that are acidic in nature, are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the acidic compounds of formula 1. Such non-toxic base salts include those derived from such pharmacologically acceptable cations as sodium, potassium calcium and magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product.

The compounds of the present invention are inhibitors of the vascular endothelial growth factor receptor ("VEGFR"), erbB family of oncogenic and protooncogenic protein tyrosine kinases such as epidermal growth factor receptor (EGFR), erbB2, HER3, or HER4 and thus are all adapted to therapeutic use as antiproliferative agents (e.g., anticancer) in mammals, particularly in humans. The compounds of the present invention are also inhibitors of angiogenesis and/or vasculogenesis. In particular, the compounds of the present invention are useful in the prevention and treatment of a variety of human hyperproliferative disorders such as malignant and benign tumors of the liver, kidney, bladder, breast, gastric, ovarian, colorectal, prostate, pancreatic, lung, vulval, thyroid, hepatic carcinomas, sarcomas, glioblastomas, head and neck, and other hyperplastic conditions such as benign hyperplasia of the skin (e.g., psoriasis) and benign hyperplasia of the prostate (e.g., BPH). It is, in addition, expected that a compound of the present invention may possess activity against a range of leukemias and lymphoid malignancies.

The compounds of the present invention may also be useful in the treatment of additional disorders in which aberrant expression ligand/receptor interactions or activation or signalling events related to various protein tyrosine kinases, are involved. Such disorders may include those of neuronal, glial, astrocytal, hypothalamic, and other glandular, macrophagal, epithelial, stromal, and blastocoelic nature in which aberrant function, expression, activation or signalling of the erbB tyrosine kinases are involved. In addition, the compounds of the present invention may have therapeutic utility in inflammatory, angiogenic and immunologic disorders involving both identified and as yet unidentified tyrosine kinases that are inhibited by the compounds of the present invention.

The in vitro activity of the compounds of formula 1 in inhibiting the receptor tyrosine kinase (and thus subsequent proliferative response, e.g., cancer) may be determined by the following procedure. The activity of the compounds of formula 1 in vitro, can be determined by the amount of inhibition of the phosphorylation of an exogenous substrate (e.g., Lys$_3$-Gastrin or polyGluTyr (4:1) random copolymer (I. Posner et al., *J. Biol. Chem.* 267 (29), 20638–47 (1992)) on tyrosine by epidermal growth factor receptor kinase by a test compound relative to a control. Affinity purified, soluble human EGF receptor (96 ng) is obtained according to the procedure in G. N. Gill, W. Weber, *Methods in Enzymology* 146, 82–88 (1987) from A431 cells (American Type Culture Collection, Rockville, Md.) and preincubated in a microfuge tube with EGF (2 µg/ml) in phosphorylation buffer+ vanadate (PBV: 50 mM HEPES, pH 7.4; 125 mM NaCl; 24 mM MgCl$_2$; 100 µM sodium orthovanadate), in a total volume of 10 µl, for 20–30 minutes at room temperature. The test compound, dissolved in dimethylsulfoxide (DMSO), is diluted in PBV, and 10 µl is mixed with the EGFR/EGF mix, and incubated for 10–30 minutes at 30° C.

The phosphorylation reaction is initiated by addition of 20 µl $^{33}$P-ATP/substrate mix (120 µM Lys$_3$-Gastrin (sequence in single letter code for amino acids, KKKGPWLEEEEEAYGWLDF), 50 mM Hepes pH 7.4, 40 µM ATP, 2 µCi γ-[$^{33}$P]-ATP) to the EGFr/EGF mix and incubated for 20 minutes at room temperature. The reaction is stopped by addition of 10 µl stop solution (0.5 M EDTA, pH 8; 2 mM ATP) and 6 µl 2N HCl. The tubes are centrifuged at 14,000 RPM, 4° C., for 10 minutes. 35 µl of supernatant from each tube is pipetted onto a 2.5 cm circle of Whatman P81 paper, bulk washed four times in 5% acetic acid, 1 liter per wash, and then air dried. This results in the binding of substrate to the paper with loss of free ATP on washing. The [$^{33}$P] incorporated is measured by liquid scintillation counting. Incorporation in the absence of substrate (e.g., lys$_3$-gastrin) is subtracted from all values as a background and percent inhibition is calculated relative to controls without test compound present. Such assays, carried out with a range of doses of test compounds, allow the determination of an approximate IC$_{50}$ value for the in vitro inhibition of EGFR kinase activity.

The activity of the compounds of formula 1 in vivo, can be determined by the amount of inhibition of tumor growth by a test compound relative to a control. The tumor growth inhibitory effects of various compounds are measured according to the methods of Corbett T. H., et al. "Tumor Induction Relationships in Development of Transplantable Cancers of the Colon in Mice for Chemotherapy Assays, with a Note on Carcinogen Structure", *Cancer Res.*, 35, 2434–2439 (1975) and Corbett, T. H., et al., "A Mouse Colon-tumor Model for Experimental Therapy", *Cancer Chemother. Rep. (Part 2)*", 5, 169–186 (1975), with slight modifications. Tumors are induced in the left flank by s.c. injection of 1×10$^6$ log phase cultured tumor cells (human MDA-MB-468 breast or human HN5 head and neck carcinoma cells) suspended in 0.10 ml RPMI 1640. After sufficient time has elapsed for the tumors to become palpable (2–3 mm in diameter) the test animals (athymic mice) are treated with active compound (formulated by dissolution in DMSO typically at a concentration of 50 to 100 mg/mL followed by 1:9 dilution into saline or, alternatively, 1:9 dilution into 0.1% Pluronic™ P105 in 0.9% saline) by the intraperitoneal (ip) or oral (po) routes of administration twice daily (i.e., every 12 hours) for 5 consecutive days. In order to determine an anti-tumor effect, the tumor is measured in millimeters with Vernier calipers across two diameters and the tumor size (mg) is calculated using the formula: Tumor weight=(length×[width]$^2$)/2, according to the methods of Geran, R. I., et al. "Protocols for Screening Chemical Agents and Natural Products Against Animal Tumors and Other Biological Systems", Third Edition, *Cancer Chemother. Rep.*, 3, 1–104 (1972). Results are expressed as percent inhibition, according to the formula: Inhibition (%)=(TuW$_{control}$-TuW$_{test}$)/TuW$_{control}$×100%. The flank site of tumor implantation provides reproducible dose/response effects for a variety of chemotherapeutic agents, and the method of measurement (tumor diameter) is a reliable method for assessing tumor growth rates.

Other methods of assessing the activity of the compounds of the present invention are referred to in PCT international application publication number WO 95/21613 (published Aug. 17, 1995) which is incorporated herein by reference.

The in vitro activity of the compounds of formula 1 in inhibiting the KDR/VEGF receptor may be determined by the following procedure.

The ability of the compounds of the present invention to inhibit tyrosine kinase activity may be measured using a recombinant enzyme in an assay that measures the ability of compounds to inhibit the phosphorylation of the exogenous substrate, polyGluTyr (PGT, Sigma™, 4:1). The kinase domain of the human KDR/VEGF receptor (amino acids 805–1350) is expressed in Sf9 insect cells as a glutathione S-transferase (GST)-fusion protein using the baculovirus expression system. The protein is purified from the lysates of these cells using glutathione agarose affinity columns. The enzyme assay is performed in 96-well plates that are coated with the PGT substrate (0.625 µg PGT per well). Test compounds are diluted in dimethylsulfoxide (DMSO), and then added to the PGT plates so that the final concentration of DMSO in the assay is 1.6% (v/v). The recombinant enzyme is diluted in phosphorylation buffer (50 mM Hepes, pH 7.3, 125 mM NaCl, 24 mM $MgCl_2$). The reaction is initiated by the addition of ATP to a final concentration of 10 µM. After a 30 minute incubation at room temperature with shaking, the reaction is aspirated, and the plates are washed with wash buffer (PBS-containing 0.1% Tween-20). The amount of phosphorylated PGT is quantitated by incubation with a HRP-conjugated (HRP is horseradish peroxidase) PY-54 antibody (Transduction Labs), developed with TMB peroxidase (TMB is 3,3',5,5'-tetramethylbenzidine), and the reaction is quantitated on a BioRad™ Microplate reader at 450 nM. Inhibition of the kinase enzymatic activity by the test compound is detected as a reduced absorbance, and the concentration of the compound that is required to inhibit the signal by 50% is reported as the $IC_{50}$ value for the test compound.

To measure the ability of the compounds to inhibit KDR tyrosine kinase activity for the full length protein that exists in a cellular context, the porcine aortic endothelial (PAE) cells transfected with the human KDR (Waltenberger et al., J. Biol. Chem. 269:26988, 1994) may be used. Cells are plated and allowed to attach to 96-well dishes in the same media (Ham's F12) with 10% v/v FBS (fetal bovine serum). The cells are then washed, re-fed with serum depleted media (0.1% v/v FBS) that contains 0.1% (v/v) bovine serum albumin (BSA), and allowed to incubate for 16–24 hours. Immediately prior to dosing with compound, the cells are re-fed with the serum depleted media (0.1% v/v FBS) (without BSA). Test compounds, dissolved in DMSO, are diluted into the media (final DMSO concentration 0.5% (v/v)). At the end of a 2 hour incubation, $VEGF_{165}$ (50 ng/ml final) is added to the media for an 8 minute incubation. The cells are washed and lysed in 50µ lysis buffer containing 20 mM Tris-HCL (pH 8), 150 mM NaCl, 1% v/v NP40, 2 mM $NaVO_4$, 500 µM EDTA, 1 mM PMSF, and 1 tablet/25 ml EDTA free complete® Protease Inhibitor Table, Roche. The cell lysates is then diluted to a final volume of 150 µl in PBS/1 mM $NaVO_4$. The extent of phosphorylation of KDR is measured using an ELISA assay. Reactibind Goat-anti Rabbit plates (Pierce) are blocked with Superblock buffer (Pierce) prior to addition of the anti-flk-1 C-20 antibody (0.5 µg per well, Santa Cruz). Any unbound antibody is washed off the plates prior to addition of 100 µl cell lysate. After a 2 hour incubation of the lysates with the flk-1 antibody, the KDR associated phosphotyrosine is quantitated by development with the HRP-conjugated PY-54 antibody and TMB, as described above. The ability of the compounds to inhibit the VEGF-stimulated autophosphorylation reaction by 50%, relative to VEGF-stimulated controls is reported as the $IC_{50}$ value for the test compound.

The ability of the compounds to inhibit mitogenesis in human endothelial cells is measured by their ability to inhibit $^3$H-thymidine incorporation into HUVE cells (human umbilical vein endothelial cells, Clonetics™). This assay has been well described in the literature (Waltenberger J et al. J. Biol. Chem. 269: 26988, 1994; Cao Y et al. J. Biol. Chem. 271: 3154, 1996). Briefly, $10^4$ cells are plated in collagen-coated 24-well plates and allowed to attach. Cells are re-fed in serum-free media, and 24 hours later are treated with various concentrations of compound (prepared in DMSO, final concentration of DMSO in the assay is 0.2% v/v), and 2–30 ng/ml $VEGF_{165}$. During the last 3 hours of the 24 hour compound treatment, the cells are pulsed with $^3$H thymidine (NEN, 1 µCi per well). The media are then removed, and the cells washed extensively with ice-cold Hank's balanced salt solution, and then 2 times with ice cold trichloroacetic acid (10% v/v). The cells are lysed by the addition of 0.2 ml of 0.1 N NaOH, and the lysates transferred into scintillation vials. The wells are then washed with 0.2 ml of 0.1 N HCl, and this wash is then transferred to the vials. The extent of $^3$H thymidine incorporation is measured by scintillation counting. The ability of the compounds to inhibit incorporation by 50%, relative to control (VEGF treatment with DMSO vehicle only) is reported as the $IC_{50}$ value for the test compound.

Administration of the compounds of the present invention (hereinafter the "active compound(s)") can be effected by any method that enables delivery of the compounds to the site of action. These methods include oral routes, intraduodenal routes, parenteral injection (including intravenous, subcutaneous, intramuscular, intravascular or infusion), topical, and rectal administration.

The amount of the active compound administered will be dependent on the subject being treated, the severity of the disorder or condition, the rate of administration and the judgement of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to about 7 g/day, preferably about 0.2 to about 2.5 g/day. In some instances, dosage levels below the lower limit of the aforesaid range may be more than adequate, while in other cases still larger doses may be employed without causing any harmful side effect, provided that such larger doses are first divided into several small doses for administration throughout the day.

The active compound may be applied as a sole therapy or may involve one or more other anti-tumour substances, for example those selected from, for example, mitotic inhibitors, for example vinblastine; alkylating agents, for example cis-platin, carboplatin and cyclophosphamide; antimetabolites, for example 5-fluorouracil, cytosine arabinoside and hydroxyurea, or, for example, one of the preferred anti-metabolites disclosed in European Patent Application No. 239362 such as N-(5-[N-(3,4-dihydro-2-methyl-4-oxoquinazolin-6-ylmethyl)-N-methylamino]-2-thenoyl)-L-glutamic acid; growth factor inhibitors; cell cycle inhibitors; intercalating antibiotics, for example adriamycin and bleomycin; enzymes, for example interferon; and anti-hormones, for example anti-estrogens such as Nolvadex™ (tamoxifen) or, for example anti-androgens such as Casodex™ (4'-cyano-3-(4-fluorophenylsulphonyl)-2-hydroxy-2-methyl-3'-trifluoromethyl)propionanilide). Such conjoint treatment may be achieved by way of the simultaneous, sequential or separate dosing of the individual components of the treatment.

The pharmaceutical composition may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound according to the invention as an active ingredient. In addition, it may include other medicinal or pharmaceutical agents, carriers, adjuvants, etc.

Exemplary parenteral administration forms include solutions or suspensions of active compounds in sterile aqueous solutions, for example, aqueous propylene glycol or dextrose solutions. Such dosage forms can be suitably buffered, if desired.

Suitable pharmaceutical carriers include inert diluents or fillers, water and various organic solvents. The pharmaceutical compositions may, if desired, contain additional ingredients such as flavorings, binders, excipients and the like. Thus for oral administration, tablets containing various excipients, such as citric acid may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Preferred materials, therefor, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

Methods of preparing various pharmaceutical compositions with a specific amount of active compound are known, or will be apparent, to those skilled in this art. For examples, see *Remington's Pharmaceutical Sciences*, Mack Publishing Company, Easter, Pa., 15th Edition (1975).

The examples and preparations provided below further illustrate and exemplify the compounds of the present invention and methods of preparing such compounds. It is to be understood that the scope of the present invention is not limited in any way by the scope of the following examples and preparations.

The examples and preparations provided below further illustrate and exemplify the compounds of the present invention and methods of preparing such compounds. It is to be understood that the scope of the present invention is not limited in any way by the scope of the following examples and preparations.

Where HPLC chromatography is referred to in the preparations and examples below, the general conditions used, unless otherwise indicated, are as follows. The column used is a ODS Hypersil column (manufactured by Hewlett Packard) of 150 mm length and 4.0 mm interior diameter. The samples are run on a Hewlett Packard-1050 system. A gradient solvent method is used running 100 percent ammonium acetate/acetic acid buffer (0.2 M) to 100 percent acetonitrile over 10 minutes. The system then proceeds on a wash cycle with 100 percent acetonitrile for 1.5 minutes and then 100 percent buffer solution for 3 minutes. The flow rate over this period is a constant 3 ml/minute. Peak detection is carried out with a diode array detector at 254 and 300 nM wavelengths.

EXAMPLE 1

A. Lithium 7-chloro-thieno[3,2-b]pyridine-2-carboxylate n-Butyllithium (0.13 mol, 52 mL) was added dropwise to a solution of 7-chloro-thieno[3,2-b]pyridine (20 g, 0.12 mol) in THF (200 mL) at −78° C., and the internal temperature was kept below −70° C. After 1 h the yellow solution was quenched with $CO_{2(g)}$ until a white suspension resulted. The resulting mixture was allowed to warm to room temperature, then concentrated under reduced pressure to give a white solid. The resulting solid was triturated with ether then dried in-vacuo to afford the title compound as a white solid (23.5 g, 90%). MS: 213 (MH+); HPLC Rf: 2.50 min; HPLC purity: 94%.

B. (7-chloro-thieno[3,2-b]pyridin-2-yl)-pyrrolidin-1-yl-methanone

A solution of lithium 7-chloro-thieno[3,2-b]pyridine-2-carboxylate (0.50 g, 2.4 mmol), thionyl chloride (3.5 mmol, 1.8 ml), $CH_2Cl_2$ (20 ml), and DMF (0.2 ml) was heated to reflux. After 3 h the resulting yellow solution was concentrated under reduced pressure, and the residue was suspended in $CH_2Cl_2$ (20 mL). Pyrrolidine (2.35 mmol, 167 mg) was then added dropwise. After 12h the reaction mixture was concentrated onto silica gel (5 mL) and purified by flash chromatography on silica gel eluting with $CH_2Cl_2$/MeOH (97/3) to afford the title compound as a white solid (360 mg, 57%). MS: 266.9/268.9 (MH+); HPLC Rf: 4.51 min; HPLC purity: 98%.

C. [7-(2-Methyl-1H-indol-5-ylamino)-thieno[3,2-b]pyridin-2-yl]-pyrrolidin-1-yl-methanone A solution of (7-chloro-thieno[3,2-b]pyridin-2-yl)-pyrrolidin-1-yl-methanone (0.359 g, 1.34 mmol) and 2-methyl-1H-indol-5-ylamine (0.19 g, 1.3 mmol) in EtOH (10 mL) was heated to reflux for 48 h. The reaction mixture was cooled to room temperature and concentrated onto silica gel (5 mL). Purification by flash chromatography on silica gel eluting with $CH_2Cl_2$/$NEt_3$ (99.5/0.5) afforded the title compound as a yellow solid (550 mg) MS: 377.2 (MH+); HPLC Rf: 4.45 min; HPLC purity: 97%.

EXAMPLE 2

A. 7-Chloro-thieno[3,2-b]pyridine-2-carboxylic acid ethylamide

The title compound was prepared from ethylamine and lithium 7-chloro-thieno[3,2-b]pyridine-2-carboxylate by a procedure analogous to Example 1B. MS: n.d.; HPLC Rf: 4.18 min; HPLC purity: 98%.

B. 7-(2-Methyl-1H-indol-5-ylamino)-thieno[3,2-b]pyridine-2-carboxylic acid ethylamide The title compound was prepared from 2-methyl-1H-indol-5-ylamine and 7-Chloro-thieno[3,2-b]pyridine-2-carboxylic acid ethylamide by a procedure analogous to Example 1C. MS: 351 (MH+); HPLC Rf: 4.33 min; HPLC purity: 98%.

EXAMPLE 3

A. 7-Chloro-thieno[3,2-b]pyridine-2-carboxylic acid amide

A solution of lithium 7-chloro-thieno[3,2-b]pyridine-2-carboxylate (1.0 g, 4.7 mmol), thionyl chloride (7.0 mmol, 3.5 mL), $CH_2Cl_2$ (40 mL), and DMF (0.4 mL) was heated to reflux. After 3 h the resulting yellow solution was concentrated under reduced pressure, the resulting residue was suspended in $CH_2Cl_2$ (60 mL), and $NH_3$ gas was bubbled through the mixture for 10 min. The reaction mixture was filtered to give the title compound as a white solid (1.17 g, 100%). MS: 213.0/215.1 (MH+); HPLC Rf: 3.44 min; HPLC purity: 98%.

B. 7-(2-Methyl-1H-indol-5-ylamino)-thieno[3,2-b]pyridine-2-carboxylic acid amide The title compound was prepared from 2-methyl-1H-indol-5-ylamine and 7-chloro-thieno[3,2-b]pyridine-2-carboxylic acid amide by a procedure analogous to Example 1C. MS: 323 (MH+); HPLC Rf: 3.65 min; HPLC purity: 98%.

EXAMPLE 4

A. 7-Chloro-thieno[3,2-b]pyridine-2-carboxylic acid dimethylamide

The title compound was prepared from dimethyl amine and lithium 7-chloro-thieno[3,2-b]pyridine-2-carboxylate by a procedure analogous to Example 1B. MS: 239/241 (MH+); HPLC Rf: n.d.; HPLC purity: n.d.

B. 7-(2-Methyl-1H-indol-5-ylamino)-thieno[3,2-b]pyridine-2-carboxylic acid dimethylamide The title compound was prepared from 2-methyl-1H-indol-5-ylamine and 7-chloro-thieno[3,2-b]pyridine-2-carboxylic acid dimethylamide by a procedure analogous to Example 1C. MS: 351 (MH+); HPLC Rf: 3.87 min.; HPLC purity: 94%.

EXAMPLE 5

A. 7-Chloro-thieno[3,2-b]pyridine-2-carboxylic acid (pyridin-3-ylmethyl)-amide

The title compound was prepared from 3-aminomethylpyridine and lithium 7-chloro-thieno[3,2-b]pyridine-2-carboxylate by a procedure analogous to Example 1B. MS: n.d.; HPLC Rf: n.d.; HPLC purity: n.d.

B. 7-(2-Methyl-1H-indol-5-ylamino)-thieno[3,2-b]pyridine-2-carboxylic acid (pyridin-3-ylmethyl)-amide The title compound was prepared from 2-methyl-1H-indol-5-ylamine and 7-chloro-thieno[3,2-b]pyridine-2-carboxylic acid (pyridin-3-ylmethyl)-amide by a procedure analogous to Example 1C. MS: 414 (MH+), HPLC Rf: 4.12 min.; HPLC purity: 97%.

EXAMPLE 6

A. 7-Chloro-thieno[3,2-b]pyridine-2-carboxylic acid methylamide

The title compound was prepared from methylamine and lithium 7-chloro-thieno[3,2-b]pyridine-2-carboxylate by a procedure analogous to Example 1B. MS: n.d.; HPLC Rf: 3.70 min.; HPLC purity: 89%.

B. 7-(2-Methyl-1H-indol-5-ylamino)-thieno[3,2-b]pyridine-2-carboxylic acid methylamide The title compound was prepared from 2-methyl-1H-indol-5-ylamine and 7-Chloro-thieno[3,2-b]pyridine-2-carboxylic acid methylamide by a procedure analogous to Example 1C. MS: 337 (MH+); HPLC Rf: 3.86 min.; HPLC purity: 98%.

EXAMPLE 7

A. 7-Chloro-thieno[3,2-b]pyridine-2-carboxylic acid (pyridin-2-ylmethyl)-amide

The title compound was prepared from 2-aminomethylpyridine and lithium 7-chloro-thieno[3,2-b]pyridine-2-carboxylate by a procedure analogous to Example 1B. MS: 304/306 (MH+); HPLC Rf: 4.36 min.; HPLC purity: 97%.

B. 7-(2-Methyl-1H-indol-5-ylamino)-thieno[3,2-b]pyridine-2-carboxylic acid (pyridin-2-ylmethyl)-amide The title compound was prepared from 2-methyl-1H-indol-5-ylamine and 7-chloro-thieno[3,2-b]pyridine-2-carboxylic acid (pyridin-2-ylmethyl)-amide by a procedure analogous to Example 1C. MS: 414 (MH+); HPLC Rf: 4.34 min.; HPLC purity: 97%.

EXAMPLE 8

A. 7-Chloro-thieno[3,2-b]pyridine-2-carboxylic acid (2-dimethylamino-ethyl)-amide The title compound was prepared from 2-dimethylaminoethyl amine and lithium 7-chloro-thieno[3,2-b]pyridine-2-carboxylate by a procedure analogous to Example 1B. MS: 284/286 (MH+); HPLC Rf: 3.47 min.; HPLC purity: 95%.

B. 7-(2-Methyl-1H-indol-5-ylamino)-thieno[3,2-b]pyridine-2-carboxylic acid (2-dimethylamino-ethyl)-amide The title compound was prepared from 2-methyl-1H-indol-5-ylamine and 7-chloro-thieno[3,2-b]pyridine-2-carboxylic acid (2-dimethylamino-ethyl)-amide by a procedure analogous to Example 1C. MS: 394 (MH+), HPLC Rf: 3.43; HPLC purity: 98%.

EXAMPLE 9

A. 7-Chloro-thieno[3,2-b]pyridine-2-carboxylic acid [3-(4-methyl-piperazin-1-yl)-propyl]-amide The title compound was prepared from 3-(4-methylpiperazin-1-yl)-propylamine and lithium 7-chloro-thieno[3,2-b]pyridine-2-carboxylate by a procedure analogous to Example 1B. MS: 353/355 (MH+); HPLC Rf: n.d.; HPLC purity: n.d.

B. 7-(2-Methyl-1H-indol-5-ylamino)-thieno[3,2-b]pyridine-2-carboxylic acid [3-(4-methyl-piperazin-1-yl)-propyl]-amide The title compound was prepared from 2-methyl-1H-indol-5-ylamine and 7-chloro-thieno[3,2-b]pyridine-2-carboxylic acid [3-(4-methyl-piperazin-1-yl)-propyl]-amide by a procedure analogous to Example 1C. MS: 463 (MH+), HPLC Rf: 3.41 min.; HPLC purity: 99%.

EXAMPLE 10

A. 7-Chloro-thieno[3,2-b]pyridine-2-carboxylic acid (3-morpholin-4-yl-propyl)-amide The title compound was prepared from 3-morpholin-4-ylpropylamine and lithium 7-chloro-thieno[3,2-b]pyridine-2-carboxylate by a procedure analogous to Example 1B. MS: 340/342 (MH+); HPLC Rf: 3.45 min.; HPLC purity: 89%.

B. 7-(2-Methyl-1H-indol-5-ylamino)-thieno[3,2-b]pyridine-2-carboxylic acid (3-morpholin-4-yl-propyl)-amide The title compound was prepared from 2-methyl-1H-indol-5-ylamine and 7-chloro-thieno[3,2-b]pyridine-2-carboxylic acid (3-morpholin-4-yl-propyl)-amide by a procedure analogous to Example 1C. MS: 450 (MH+); HPLC Rf: 3.48 min.; HPLC purity 96%.

EXAMPLE 11

A. 7-Chloro-thieno[3,2-b]pyridine-2-carboxylic acid (pyridin-4-ylmethyl)-amide

The title compound was prepared from 4-aminomethyl pyridine and lithium 7-chloro-thieno[3,2-b]pyridine-2- carboxylate by a procedure analogous to Example 1B. MS: 304/306 (MH+); HPLC Rf: 4.08 min.; HPLC purity: 78%.

B. 7-(2-Methyl-1H-indol-5-ylamino)-thieno[3,2-b] pyridine-2-carboxylic acid (pyridin-4-ylmethyl)-amide The title compound was prepared from 2-methyl-1H-indol-5-ylamine and 7-chloro-thieno[3,2-b]pyridine-2-carboxylic acid (pyridin-4-ylmethyl)-amide by a procedure analogous to Example 1C. MS: 414 (MH+), HPLC Rf: 3.97 min.; HPLC purity 94%.

EXAMPLE 12

A. 7-Chloro-thieno[3,2-b]pyridine-2-carboxylic acid (2-pyridin-2-yl-ethyl)-amide The title compound was prepared from 2-pyridine-2-yl-ethylamine pyridine and lithium 7-chloro-thieno[3,2-b]pyridine-2-carboxylate by a procedure analogous to Example 1B. MS: 318/320 (MH+); HPLC Rf: 4.33 min.; HPLC purity: 97%.

B. 7-(2-Methyl-1H-indol-5-ylamino)-thieno[3,2-b] pyridine-2-carboxylic acid (2-pyridin-2-yl-ethyl)-amide The title compound was prepared from 2-methyl-1H-indol-5-ylamine and 7-chloro-thieno[3,2-b]pyridine-2-carboxylic acid (2-pyridin-2-yl-ethyl)-amide by a procedure analogous to Example 1C. MS: 428 (MH+), HPLC Rf: 4.33 min; HPLC purity 99%.

EXAMPLE 13

A. 7-Chloro-thieno[3,2-b]pyridine-2-carboxylic acid pyridin-4-ylamide

The title compound was prepared from 4-aminopyridine and lithium 7-chloro-thieno[3,2-b]pyridine-2-carboxylate by a procedure analogous to Example 1B. MS: 290/292 (MH+); HPLC Rf: 4.63 min.; HPLC purity: 99%.

B. 7-(2-Methyl-1H-indol-5-ylamino)-thieno[3,2-b] pyridine-2-carboxylic acid pyridin-4-ylamide The title compound was prepared from 2-methyl-1H-indol-5-ylamine and 7-chloro-thieno[3,2-b]pyridine-2-carboxylic acid pyridin-4-ylamide by a procedure analogous to Example 1C. MS: 400 (MH+); HPLC Rf: 4.24 min.; HPLC purity: 99%.

EXAMPLE 14

A. 7-Chloro-thieno[3,2-b]pyridine-2-carboxylic acid (2-morpholin-4-yl-ethyl)-amide The title compound was prepared from 2-morpholine-4-yl-ethylamine and lithium 7-chloro-thieno[3,2-b]pyridine-2-carboxylate by a procedure analogous to Example 1B. MS: 326/328 (MH+); HPLC Rf: 3.45 min.; HPLC purity 94%.

B. 7-(2-Methyl-1H-indol-5-ylamino)-thieno[3,2-b] pyridine-2-carboxylic acid (2-morpholin-4-yl-ethyl)-amide The title compound was prepared from 2-methyl-1H-indol-5-ylamine and 7-chloro-thieno[3,2-b]pyridine-2-carboxylic acid (2-morpholin-4-yl-ethyl)-amide by a procedure analogous to Example 1C. MS: 436 (MH+); HPLC Rf: 3.45 min.; HPLC purity 94%.

EXAMPLE 15

A. 7-Chloro-thieno[3,2-b]pyridine-2-carboxylic acid (2-pyridin-4-yl-ethyl)-amide The title compound was prepared from 2-pyridin-4-yl-ethyl amine and lithium 7-chloro-thieno[3,2-b]pyridine-2-carboxylate by a procedure analogous to Example 1B. MS: 318/320 (MH+); HPLC Rf: 4.08 min.; HPLC purity 99%.

B. 7-(2-Methyl-1H-indol-5-ylamino)-thieno[3,2-b] pyridine-2-carboxylic acid (2-pyridin-4-yl-ethyl)-amide The title compound was prepared from 2-methyl-1H-indol-5-ylamine and 7-chloro-thieno[3,2-b]pyridine-2-carboxylic acid (2-pyridin-4-yl-ethyl)-amide by a procedure analogous to Example 1C. MS: 428 (MH+); HPLC Rf: 4.09 min.; HPLC purity 99%.

EXAMPLE 16

A. 7-Chloro-thieno[3,2-b]pyridine-2-carboxylic acid (2-piperidin-1-yl-ethyl)-amide The title compound was prepared from 2-piperidin-1-yl-ethyl amine and lithium 7-chloro-thieno[3,2-b]pyridine-2-carboxylate by a procedure analogous to Example 1B. MS: 324/326 (MH+); HPLC Rf: 3.64 min.; HPLC purity 93%.

B. 7-(2-Methyl-1H-indol-5-ylamino)-thieno[3,2-b] pyridine-2-carboxylic acid (2-piperidin-1-yl-ethyl)-amide The title compound was prepared from 2-methyl-1H-indol-5-ylamine and 7-chloro-thieno[3,2-b]pyridine-2-carboxylic acid (2-piperidin-1-yl-ethyl)-amide by a procedure analogous to Example 1C. MS: 434 (MH+); HPLC Rf: 3.82 min.; HPLC purity 99%.

EXAMPLE 17

A. 7-Chloro-thieno[3,2-b]pyridine-2-carboxylic acid pyridin-3-ylamide

The title compound was prepared from 3-aminopyridine and lithium 7-chloro-thieno[3,2-b]pyridine-2-carboxylate by a procedure analogous to Example 1B. MS: 290/292 (MH+), HPLC Rf: 4.72 min.; HPLC purity 95%.

B. 7-(2-Methyl-1H-indol-5-ylamino)-thieno[3,2-b] pyridine-2-carboxylic acid pyridin-3-ylamide The title compound was prepared from 2-methyl-1H-indol-5-ylamine and 7-chloro-thieno[3,2-b]pyridine-2-carboxylic acid pyridin-3-ylamide by a procedure analogous to Example 1C. MS: 400 (MH+), HPLC Rf: 4.58 min.; HPLC purity 99%.

EXAMPLE 18

A. 7-Chloro-thieno[3,2-b]pyridine-2-carboxylic acid (2-pyridin-3-yl-ethyl)-amide The title compound was prepared from 2-pyridine-3-yl-ethyl amine and lithium 7-chloro-thieno[3,2-b]pyridine-2-carboxylate by a procedure analogous to Example 1B. MS: 318/320 (MH+); HPLC Rf: 4.27 min.; HPLC purity 76%.

B. 7-(2-Methyl-1H-indol-5-ylamino)-thieno[3,2-b] pyridine-2-carboxylic acid (2-pyridin-3-yl-ethyl)-amide The title compound was prepared from 2-methyl-1H-indol-5-ylamine and 7-chloro-thieno[3,2-b]pyridine-2-carboxylic acid (2-pyridin-3-yl-ethyl)-amide by a procedure analogous to Example 1C. MS: 428 (MH+); HPLC Rf: 4.34 min.; HPLC purity 99%.

EXAMPLE 19

A. 7-Chloro-thieno[3,2-b]pyridin-2-yl-morpholin-4-yl-methanone

The title compound was prepared from morpholine and lithium 7-chloro-thieno[3,2-b]pyridine-2-carboxylate by a procedure analogous to Example 1B. MS: 282/284 (MH+), HPLC Rf: 3.96 min.; HPLC purity 98%.

B. [7-(2-Methyl-1H-indol-5-ylamino)-thieno[3,2-b] pyridin-2-yl]-morpholin-4-yl-methanone The title compound was prepared from 2-methyl-1H-indol-5-ylamine and 7-chloro-thieno[3,2-b]pyridin-2-ylmorpholin-4-yl-methanone by a procedure analogous to Example 1C. MS: 393 (MH+), HPLC Rf: 3.90 min.; HPLC purity 96%.

EXAMPLE 20

A. 7-Chloro-thieno[3,2-b]pyridine-2-carbonitrile n-Butyllithium (2.2 mmol, 0.88 mL) was added dropwise to a solution of 7-chloro-thieno[3,2-b]pyridine (0.250 g, 1.48 mmol) in THF (10 mL) at −78° C. while the internal temperature was kept below −70° C. After 1 h TsCN (0.804 mg, 4.44 mmol) was added. After 3 h the reaction was quenched with distilled water (10 mL), warmed to rt, and the layers were separated. The aqueous layer was further extracted with ethyl acetate (3×10 mL). The combined organic extracts were dried (Na$_2$SO$_4$), then concentrated under reduced pressure. Purification by flash chromatography using a Biotage 40 S column eluting with hexane/ethyl acetate (7/3) afforded the title compound as a white solid (92 mg, 32%). MS: 195/197 (MH+); HPLC Rf: 4.89 min; HPLC purity: 85%.

B. 7-(2-Methyl-1H-indol-5-ylamino)-thieno[3,2-b]pyridine-2-carbonitrile

The title compound was prepared from 2-methyl-1H-indol-5-ylamine and 7-chloro-thieno[3,2-b]pyridine-2-carbonitrile by a procedure analogous to Example 1C. MS: 305 (MH+), HPLC Rf: 4.86 min.; HPLC purity: 85%.

EXAMPLE 21

A. 7-(2-Methyl-1H-indol-5-ylamino)-thieno[3,2-b]pyridine-2-carboxylic acid

Lithium 7-chloro-thieno[3,2-b]pyridine-2-carboxylate carboxylate (1.00 g, 4.68 mmole) and 2-methyl-1H-indol-5-ylamine (822 mg, 5.62 mmole) were dissolved in a mixture of ethanol (90 mL) and dichloroethane (10 mL). The reaction mixture was heated at reflux for 40 hours. Upon cooling, a yellow precipitate formed, which was collected by filtration and washed with ether. After drying under vacuum, the title compound was obtained as yellow powder (1.13 g, 75%). MS: 324 (MH+); HPLC Rf: 3.10min; HPLC purity: 97%.

B. (+/−)-(3-Hydroxy-pyrrolidin-1-yl)[7-(2-methyl-1H-indol-5-ylamino)-thieno[3,2-b]pyridin-2-yl]-methanone To a solution of 7-(2-methyl-1H-indol-5-ylamino)-thieno[3,2-b]pyridine-2-carboxylic acid (0.10 g, 0.31 mmol), HATU (0.17 g, 0.46 mmol) and DMAP (0.040 g, 0.31 mmol) in DMF (3 mL) was added racemic 3-hydroxy-pyrrolidine (0.040 g, 0.46 mmol). After 3 h the reaction was quenched with a saturated aqueous solution of NaHCO$_3$ (10 mL) and EtOAC (10 mL). The aquenched layer was further extracted with EtOAC (2×10 mL). The combined organic extracts were dried (Na$_2$SO$_4$) and concentrated under reduced pressure. Purification by flash chromatography on silica gel (CH$_2$Cl$_2$/MeOH 85:15) afforded the title compound as a yellow solid (0.093 g, 76%). MS: 393 (MH+); HPLC Rf: 3.41; HPLC purity: 87%.

EXAMPLES 22–60

Compounds from examples 22–60 were synthesized by one of two methods. Method A is a two-step method analogous to that described in Example 1B/C. In each case, a commercially available amine was coupled to lithium 7-chloro-thieno[3,2-b]pyridine-2-carboxylate by a procedure analogous to Example 1B, and the resulting amides were treated with 2-methyl-1H-indole-5-ylamine according to Example 1C to give the title compounds. Method B involves the coupling of an amine to 7-(2-methyl-1H-indol-5-ylamino)-thieno[3,2-b]pyridine-2-carboxylic acid by a method analogous to Example 21B.

| Example Number | Compound Name | Method | MS (MH+) | HPLC purity | HPLC Rf (min) |
|---|---|---|---|---|---|
| 22 | 7-(2-Methyl-1H-indol-5-ylamino)-thieno[3,2-b]pyridine-2-carboxylic acid methyl-pyridin-3-ylmethyl-amide | A | 428 | 93 | 4.08 |
| 23 | [7-(2-Methyl-1H-indol-5-ylamino)-thieno[3,2-b]pyridin-2-yl]-(4-methyl-piperazin-1-yl)-methanone | A | 406 | 99 | 3.13 |
| 24 | 7-(2-Methyl-1H-indol-5-ylamino)-thieno[3,2-b]pyridine-2-carboxylic acid thiazol-2-ylamide | A | 406 | 98 | 4.79 |
| 25 | 7-(2-Methyl-1H-indol-5-ylamino)-thieno[3,2-b]pyridine-2-carboxylic acid diethylamide | A | 379 | 95 | 4.54 |
| 26 | 7-(2-Methyl-1H-indol-5-ylamino)-thieno[3,2-b]pyridine-2-carboxylic acid ethyl-methyl-amide | A | 365 | 97 | 4.15 |
| 27 | Azetidin-1-yl-[7-(2-methyl-1H-indol-5-ylamino)-thieno[3,2-b]pyridin-2-yl]-methanone | A | 363 | 99 | 4.07 |
| 28 | (3,4-Dihydro-1H-isoquinolin-2-yl)-[7-(2-methyl-1H-indol-5-ylamino)-thieno[3,2-b]pyridin-2-yl]-methanone | AA | 439 | 98 | 5.47 |
| 29 | CP-702055-01: 7-(2-Methyl-1H-indol-5-ylamino)-thieno[3,2-b]pyridine-2-carboxylic acid (2-dimethylamino-ethyl)-methyl-amide | A | 408 | 99 | 3.37 |
| 30 | 7-(2-Methyl-1H-indol-5-ylamino)-thieno[3,2-b]pyridine-2-carboxylic acid cyclohexyl-methyl-amide | A | 419 | 98 | 5.47 |
| 31 | 7-(2-Methyl-1H-indol-5-ylamino)-thieno[3,2-b]pyridine-2-carboxylic acid cyclohexylamide | A | 405 | 98 | 5.74 |
| 32 | Aziridin-1-yl-[7-(2-methyl-1H-indol-5-ylamino)-thieno[3,2-b]pyridin-2-yl]-methanone | A | 349 | 99 | 4.60 |

-continued

| Example Number | Compound Name | Method | MS (MH+) | HPLC purity | HPLC Rf (min) |
|---|---|---|---|---|---|
| 33 | (2S)-(2-Methoxymethyl-pyrrolidin-1-yl)-[7-(2-methyl-1H-indol-5-ylamino)-thieno[3,2-b]pyridin-2-yl]-methanone | A | 421 | 99 | 4.55 |
| 34 | (2,5-Dimethyl-pyrrolidin-1-yl)-[7-(2-methyl-1H-indol-5-ylamino)-thieno[3,2-b]pyridin-2-yl]-methanone | A | 405 | 95 | 5.28 |
| 35 | (2,6-Dimethyl-piperidin-1-yl)-[7-(2-methyl-1H-indol-5-ylamino)-thieno[3,2-b]pyridin-2-yl]-methanone | A | 419 | 95 | 5.43 |
| 36 | (+/−)-N-{1-[7-(2-Methyl-1H-indol-5-ylamino)-thieno[3,2-b]pyridine-2-carbonyl]-pyrrolidin-3-yl}-acetamide | A | 434 | 93 | 3.72 |
| 37 | (+/−)-N-Ethyl-N-{1-[7-(2-methyl-1H-indol-5-ylamino)-thieno[3,2-b]pyridine-2-carbonyl]-pyrrolidin-3-yl}-acetamide | A | 462 | 92 | 4.14 |
| 38 | CP-708103-01: 7-(2-Methyl-1H-indol-5-ylamino)-thieno[3,2-b]pyridine-2-carboxylic acid diisopropylamide | A | 407 | 98 | 5.66 |
| 39 | 1-[7-(2-Methyl-1H-indol-5-ylamino)-thieno[3,2-b]pyridine-2-carbonyl]-(2S)-pyrrolidine-2-carboxylic acid amide | A | 420 | 95 | 3.47 |
| 40 | [7-(2-Methyl-1H-indol-5-ylamino)-thieno[3,2-b]pyridin-2-yl]-thiomorpholin-4-yl-methanone | A | 409 | 95 | 4.72 |
| 41 | (+/−)-1-[7-(2-Methyl-1H-indol-5-ylamino)-thieno[3,2-b]pyridine-2-carbonyl]-piperidine-3-carboxylic acid ethyl ester | A | 463 | 97 | 5.17 |
| 42 | (+/−)-(3-Methylamino-pyrrolidin-1-yl)-[7-(2-methyl-1H-indol-5-ylamino)-thieno[3,2-b]pyridin-2-yl]-methanone | A | 406 | 90 | 3.56 |
| 43 | 1-[7-(2-Methyl-1H-indol-5-ylamino)-thieno[3,2-b]pyridine-2-carbonyl]-pyrrolidine-(2S)-2-carboxylic acid dimethylamide | A | 448 | 96 | 4.06 |
| 44 | 7-(2-Methyl-1H-indol-5-ylamino)-thieno[3,2-b]pyridine-2-carboxylic acid (2-methoxy-ethyl)-methyl-amide | A | 395 | 92 | 4.26 |
| 45 | 7-(2-Methyl-1H-indol-5-ylamino)-thieno[3,2-b]pyridine-2-carboxylic acid (2,2,2-trifluoro-ethyl)-amide | A | 405 | 98 | 5.13 |
| 46 | (3S)-(3-Dimethylamino-pyrrolidin-1-yl)-[7-(2-methyl-1H-indol-5-ylamino)-thieno[3,2-b]pyridin-2-yl]-methanone | A | 420 | 99 | 3.67 |
| 47 | (3S)-(3-Amino-pyrrolidin-1-yl)-[7-(2-methyl-1H-indol-5-ylamino)-thieno[3,2-b]pyridin-2-yl]-methanone | A | 392 | 99 | 3.30 |
| 48 | 1-[7-(2-Methyl-1H-indol-5-ylamino)-thieno[3,2-b]pyridine-2-carbonyl]-pyrrolidine-(2S)-2-carboxylic acid | A | 421 | 84 | 3.32 |
| 49 | 7-(2-Methyl-1H-indol-5-ylamino)-thieno[3,2-b]pyridine-2-carboxylic acid bis-(2,2,2-trifluoro-ethyl)-amide | A | 487 | 90 | 5.74 |
| 50 | (+/−)-N-Methyl-N-{1-[7-(2-methyl-1H-indol-5-ylamino)-thieno[3,2-b]pyridine-2-carbonyl]-pyrrolidin-3-yl}-acetamide | A | 448 | 97 | 3.88 |
| 51 | (3R)-(3-Dimethylamino-pyrrolidin-1-yl)-[7-(2-methyl-1H-indol-5-ylamino)-thieno[3,2-b]pyridin-2-yl]-methanone | A | 420 | 99 | 3.82 |
| 52 | (2R)-(2-Methoxymethyl-pyrrolidin-1-yl)-[7-(2-methyl-1H-indol-5-ylamino)-thieno[3,2-b]pyridin-2-yl]-methanone | B | 421 | 96 | 4.61 |
| 53 | (+/−)-(3-Hydroxy-pyrrolidin-1-yl)-7(2-methyl-1H-indol-5-ylamino)-thieno[3,2-b]pyridin-2-yl]methanone | B | 393 | 91 | 3.57 |
| 54 | (2R)-(2-Hydroxymethylpyrrolidin-1-yl)-[7-(2-methyl-1H-indol-5-ylamino)-thieno[3,2-b]pyridin-2-yl]-methanone | B | 407 | 88 | 3.20 |
| 55 | (2S)-(2-Hydroxymethyl-pyrrolidin-1-yl)-[7-(2-methyl-1H-indol-5-ylamino)-thieno[3,2-b]pyridin-2-yl]-methanone | B | 407 | 95 | 3.47 |
| 56 | (3S)-(3-Hydroxy-pyrrolidin-1-yl)-[7-(2-methyl-1H-indol-5-ylamino)-thieno[3,2-b]pyridin-2-yl]methanone | B | 393 | 92 | 2.97 |
| 57 | (3R)-(3-Hydroxy-pyrrolidin-1-yl)-[7-(2-methyl-1H-indol-5-ylamino)-thieno[3,2-b]pyridin-2-yl]-methanone | B | 393 | 94 | 3.68 |

-continued

| Example Number | Compound Name | Method | MS (MH+) | HPLC purity | HPLC Rf (min) |
|---|---|---|---|---|---|
| 58 | (6-Hydroxymethyl-3-aza-bicyclo[3.1.0]hex-3-yl)-[7-(2-methyl-1H-indol-5-ylamino)-thieno[3,2-b]pyridin-2-yl]-methanone | B | 419 | 95 | 3.74 |
| 59 | [7-(2-Methyl-1H-indol-5-ylamino)-thieno[3,2-b]pyridin-2-yl]-piperidin-1-yl-methanone | B | 391 | 98% | 4.72 |
| 60 | (3,4-Dihydroxy-pyrrolidin-1-yl)-[7-(2-methyl-1H-indol-5-ylamino)-thieno[3,2-b]pyridin-2-yl]-methanone | B | 409 | 92 | 3.31 |

EXAMPLE 61

A. 7-Chloro-thieno[3,2-b]pyridine-2-carboxylic acid methyl-pyridin-4-ylmethyl-amide NaH (0.244 g, 6.09 mmol) was added to a solution of 7-chloro-thieno[3,2-b]pyridin-2-carboxylic acid (pyridin-4-ylmethyl)-amide (0.616 g, 2.03 mmol, prepared as described in Example 11) in DMF (10 mL). When the effervescence ceased, MeI (0.576 g, 4.06 mmol) was added dropwise. After 3 h the reaction mixture was quenched with saturated aqueous KCN (10 mL). The aqueous layer was extracted with $CH_2Cl_2$ (3×10 mL). The combined organic extracts were dried ($Na_2SO_4$), and the solvent was removed under reduced pressure. Purification by flash chromatography on silica gel ($CH_2Cl_2$/MeOH 94:6) afforded the title compound as a yellow oil (0.15 g, 23%). MS: 318.0/320.0 (MH+); HPLC Rf: 4.24 min; HPLC purity: 93%.

B. 7-(2-Methyl-1H-indol-5-ylamino)-thieno[3,2-b]pyridine-2-carboxylic acid methyl-pyridin-4-ylmethyl-amide The title compound was prepared from 7-chloro-thieno [3,2-b]pyridine-2-carboxylic acid methyl-pyridin-4-ylmethyl-amide and 2-methyl-1H-indol-5-ylamine by a method analogous to Example 1C. MS: 428 (MH+); HPLC Rf: 4.26 min; HPLC purity: 93%.

EXAMPLE 62

A. 7-Chloro-thieno[3,2-b]pyridine-2-carboxylic acid methyl-pyridin-2-ylmethyl-amide The title compound was prepared from MeI and 7-chloro-thieno[3,2-b]pyridine-2-carboxylic acid (pyridin-2-ylmethyl)-amide (Example 7A) as described in Example 61A. MS: 318/320 (MH+); HPLC Rf: 4.40 min.; HPLC purity: 90%.

B. 7-(2-Methyl-1H-indol-5-ylamino)-thieno[3,2-b]pyridine-2-carboxylic acid methyl-pyridin-2-ylmethyl-amide The title compound was prepared from 7-chloro-thieno [3,2-b]pyridine-2-carboxylic acid methyl-pyridin-2-ylmethyl-amide and 2-methyl-1H-indol-5-ylamine by a procedure analogous to Example 1C. MS: 428 (MH+); HPLC Rf: 4.30 min.; HPLC purity: 97%.

EXAMPLE 63

A. 7-Chloro-thieno[3,2-b]pyridine-2-carboxylic acid methyl-(2-morpholin-4-yl-ethyl)-amide The title compound was prepared from MeI and 7-chloro-thieno[3,2-b]pyridine-2-carboxylic acid (2-morpholin-4-yl-ethyl)-amide (Example 14A) by a procedure analogous to Example 61A. MS: 340/342 (MH+); HPLC Rf: 3.29 min.; HPLC purity 99%.

B. 7-(2-Methyl-1H-indol-5-ylamino)-thieno[3,2-b] pyridine-2-carboxylic acid methyl-(2-morpholin-4-yl-ethyl)-amide The title compound was prepared from 7-chloro-thieno [3,2-b]pyridine-2-carboxylic acid methyl-(2-morpholin-4-yl-ethyl)-amide and 2-methyl-1H-indol-5-ylamine by a procedure analogous to Example 1C. MS: 450 (MH+), HPLC Rf: 3.58 min.; HPLC purity: 99%.

EXAMPLE 64

A. (+/−)-[1-(7-Chloro-thieno[3,2-b]pyridine-2-carbonyl)-pyrrolidin-3-yl]-carbamic acid tert-butyl ester The title compound was prepared from lithium 7-chloro-thieno[3,2-b]pyridine-2-carboxylate and racemic pyrrolidin-3-yl-carbamic acid tert butyl ester by a method analogous to Example 1B. MS: 382/384 (MH+); HPLC Rf: 5.21 min.; HPLC purity 99%.

B. (+/−)-(3-Amino-pyrrolidin-1-yl)-(7-chloro-thieno[3,2-b]pyridin-2yl)-methanone HCl(g) was bubbled through a solution of [1-(7-chloro-thieno[3,2-b]pyridine-2-carbonyl)-pyrrolidin-3-yl]-carbamic acid tert-butyl ester (0.472 g, 1.23 mmol) in MeOH (10 mL). After 10 min, TLC ($CH_2Cl_2$/MeOH 9:1) showed the reaction to be complete. The reaction mixture was poured into $Et_2O$ (50 mL), and a white precipitate formed. The white solid was collected by filtration and washed with $Et_2O$ to afford the title compound. MS: 281.0/283.0 (MH+); HPLC Rf; 3.02 min; HPLC purity: 99%.

C. (+/−)-Cyclobutanecarboxylic acid {1-[7-chloro-thieno [3,2-b]pyridine-2-carbonyl]-pyrrolidin-3-yl}-amide To a solution of (3-amino-pyrrolidin-1-yl)-(7-chloro-thieno[3,2-b]pyridin-2yl)-methanone (0.40 g, 1.4 mmol) and DMAP (0.693 g, 5.68 mmol) in $CH_2Cl_2$ (20 mL) was added cyclobutane carboxylic acid chloride (0.20 g, 1.7 mmol). After 3 h the reaction was quenched with distilled water (10 mL). The aqueous layer was extracted with $CH_2Cl_2$ (2×10 mL). The combined organic extracts were dried ($Na_2SO_4$), and concentrated onto silica gel (5 mL). Purification by flash chromatography on silica gel ($CH_2Cl_2$/MeOH 97:3) afforded the title compound as a white solid (0.36 g, 69%). MS: 364/366 (MH+); HPLC Rf: 4.24 min; HPLC purity: 94%.

D. (+/−)-Cyclobutanecarboxylic acid {1-[7-(2-methyl-1H-indol-5-ylamino)-thieno[3,2-b]pyridine-2-carbonyl]-pyrrolidin-3-yl}-amide The title compound was prepared from (+/−)-cyclobutanecarboxylic acid {1-[7-chloro-thieno[3,2-b]pyridine-2-carbonyl]-pyrrolidin-3-yl}-amide and 2-methyl-1H-indol-5-ylamine by a procedure analogous to Example 1C. MS: 474 (MH+); HPLC Rf: 4.37 min.; HPLC purity 97%.

EXAMPLE 65

A. {3-[7-Chloro-thieno[3,2-b]pyridine-2-carbonyl]-3-aza-bicyclo[3.1.0]hex-6-yl}-carbamic acid tert-butyl ester The title compound was prepared from (3-aza-bicyclo[3.1.0]hex-6-yl)-carbamic acid tert-butyl ester and lithium 7-chloro-thieno[3,2-b]pyridine-2-carboxylate by a procedure analogous to Example 1B. MS: 394/396 (MH+); HPLC Rf: 5.30 min.; HPLC purity: 72%.

B. {3-[7-(2-Methyl-1H-indol-5-ylamino)-thieno[3,2-b]pyridine-2-carbonyl]-3-aza-bicyclo[3.1.0]hex-6-yl}-carbamic acid tert-butyl ester The title compound was prepared from {3-[7-chloro-thieno[3,2-b]pyridine-2-carbonyl]-3-aza-bicyclo[3.1.0]hex-6-yl}-carbamic acid tert-butyl ester and 2-methyl-1H-indol-5-ylamine by a procedure analogous to Example 1C. MS: 504 (MH+); HPLC Rf: 5.31 min.; HPLC purity 95%.

C. 6-Amino-3-aza-bicyclo[3.1.0]hex-3-yl)-[7-(2-methyl-1H-indol-5-ylamino)-thieno[3,2-b]pyridin-2-yl]-methanone The title compound was prepared by treating {3-[7-(2-methyl-1H-indol-5-ylamino)-thieno[3,2-b]pyridine-2-carbonyl]-3-aza-bicyclo[3.1.0]hex-6-yl}-carbamic acid tert-butyl ester with HCl gas as described in Example 64B. MS: 404 (MH+); HPLC Rf: 3.42 min.; HPLC purity: 97%.

EXAMPLE 66

A. 4-[7-Chloro-thieno[3,2-b]pyridine-2-carbonyl]-piperazine-1-carboxylic acid tert-butyl ester The title compound was prepared from piperazine-1-carboxylic acid tert-butyl ester and lithium 7-chloro-thieno[3,2-b]pyridine-2-carboxylate by a procedure analogous to Example 1B. MS: 382/384 (MH+); HPLC Rf: 5.72 min.; HPLC purity 94%.

B. 4-[7-(2-Methyl-1H-indol-5-ylamino)-thieno[3,2-b]pyridine-2-carbonyl]-piperazine-1-carboxylic acid tert-butyl ester The title compound was prepared from 4-[7-chloro-thieno[3,2-b]pyridine-2-carbonyl]-piperazine-1-carboxylic acid tert-butyl ester and 2-methyl-1H-indol-5-ylamine by a method analogous to Example 1C. MS: 492 (MH+); HPLC Rf: 5.42 min.; HPLC purity 95%.

C. [7-(2-Methyl-1H-indol-5-ylamino)-thieno[3,2-b]pyridin-2-yl]-piperazin-1-yl-methanone The title compound was prepared by treating 4-[7-(2-methyl-1H-indol-5-ylamino)-thieno[3,2-b]pyridine-2-carbonyl]-piperazine-1-carboxylic acid tert-butyl ester with HCl gas as described in Example 64B. MS: 392 (MH+); HPLC Rf: 3.51 min.; HPLC purity: 93%.

EXAMPLE 67

A. (+/−)-(3-Hydroxy-pyrrolidin-1-yl)-[7-chloro-thieno[3,2-b]pyridin-2-yl]-methanone This compound was prepared from (+/−)-3-hydroxypyrrolidine and lithium 7-chloro-thieno[3,2-b]pyridine-2-carboxylate by a procedure analogous to Example 1B. MS: 283/285 (MH+); HPLC Rf: 3.44 min.; HPLC purity 91%.

B. (+/−)-(3-Methoxy-pyrrolidin-1-yl)-[7-chloro-thieno[3,2-b]pyridin-2-yl]-methanone NaH (0.07 g, 1.3 mmol) was added to a solution of (+/−)-(3-hydroxy-pyrrolidin-1-yl)-[7-chloro-thieno[3,2-b]pyridin-2-yl]-methanone (0.25 g, 0.88 mmol) in DMF (10 mL), at 0° C. The reaction mixture was allowed to stir for 20 min, and MeI (0.188 g, 1.33 mmol) was added dropwise. After 3 h the reaction was quenched with saturated aqueous KCN (10 mL). The aqueous layer was extracted with CH₂Cl₂ (3×10 mL). The combined organic extracts were dried (Na₂SO₄), and the solvent was removed. Purification by flash chromatography on silica gel (CH₂Cl₂/MeOH 94:6) afforded the title compound as a white solid (0.13 g, 50%). MS: 297/299 (MH+); HPLC Rf: 4.11 min; HPLC purity: 93%.

C. (+/−)-(3-Methoxy-pyrrolidin-1-yl)-[7-(2-methyl-1H-indol-5-ylamino)-thieno[3,2-b]pyridin-2-yl]-methanone The title compound was prepared from (3-methoxy-pyrrolidin-1-yl)-[7-chloro-thieno[3,2-b]pyridin-2-yl]-methanone and 2-methyl-1H-indol-5-ylamine by a procedure analogous to Example 1C. MS: 407 (MH+); HPLC Rf: 4.22 min.; HPLC purity 96%.

EXAMPLE 68

(3R)-(3-Methoxy-pyrrolidin-1-yl)-[7-(2-methyl-1H-indol-5-ylamino)-thieno[3,2-b]pyridin-2-yl]-methanone This compound was prepared by methods analogous to Example 67, using enantiomerically pure (3R)-3-hydroxy-pyrrolidine as a starting material. MS: 407 (MH+); HPLC Rf: 4.23 min.; HPLC purity: 98%.

EXAMPLE 69

(3S)-(3-Methoxy-pyrrolidin-1-yl)-[7-(2-methyl-1H-indol-5-ylamino)-thieno[3,2-b]pyridin-2-yl]-methanone This compound was prepared by methods analogous to Example 67, using enantiomerically pure (3S)-3-hydroxy-pyrrolidine as a starting material. MS: 407 (MH+); HPLC Rf: 4.21 min.; HPLC purity: 97%.

EXAMPLE 70

A. (+/−)-[1-(7-Chloro-thieno[3,2-b]pyridine-2-carbonyl)-pyrrolidin-3-yl]-carbamic acid tert-butyl ester The title compound was prepared from lithium 7-chloro-thieno[3,2-b]pyridine-2-carboxylate and (+/−)-pyrrolidin-3-yl-carbamic acid tert butyl ester by a method analogous to Example 1B. MS: 382/384 (MH+); HPLC Rf: 5.21 min.; HPLC purity 99%.

B. (+/−)-[1-[7-(2-methyl-1H-indol-5-ylamino)-thieno[3,2-b]pyridine-2-carbonyl]-pyrrolidin-3-yl]-carbamic acid tert-butyl ester The title compound was prepared from (+/−)-[1-(7-chloro-thieno[3,2-b]pyridine-2-carbonyl)-pyrrolidin-3-yl]-carbamic acid tert-butyl ester and 2-methyl-1H-indol-5-ylamine by a procedure analogous to Example 1C. MS: 492 (MH+); HPLC Rf: 5.23 min.; HPLC purity 96%.

C. (+/−)-3-Amino-pyrrolidin-1-yl)-[7-(2-methyl-1H-indol-5-ylamino)-thieno[3,2-b]pyridin-2-yl]-methanone The title compound was prepared by treating (+/−)-[1-[7-(2-methyl-1H-indol-5-ylamino)-thieno[3,2-b]pyridine-2-carbonyl]-pyrrolidin-3-yl]-carbamic acid tert-butyl ester with HCl gas as described in Example 64B. MS: 392 (MH+); HPLC Rf: 3.30 min.; HPLC purity: 99%.

EXAMPLE 71

A. (+/−)-Dimethylsulfamic acid {1-[7-chloro-thieno[3,2-b]pyridine-2-carbonyl]-pyrrolidin-3-yl}-amide The title compound was prepared from dimethylsulfamoyl chloride and (3-amino-pyrrolidin-1-yl)-(7-chloro-thieno[3,2-b]pyridin-2yl)-methanone by a procedure analogous to Example 64C. MS: 389/391 (MH+); HPLC Rf: 4.26 min.; HPLC purity 99%.

B. (+/−)-Dimethylsulfamic acid {1-[7-(2-methyl-1H-indol-5-ylamino)-thieno[3,2-b]pyridine-2-carbonyl]-pyrrolidin-3-yl}-amide The title compound was prepared from (+/−)-dimethylsulfamic acid {1-[7-chloro-thieno[3,2-b]pyridine-2-carbonyl]-pyrrolidin-3-yl}-amide and 2-methyl-1H-indol-5-ylamine by a procedure analogous to Example 1C. MS: 499 (MH+); HPLC Rf: 4.04 min.; HPLC purity 96%.

EXAMPLE 72

A. (+/−)-Methanesulfonic acid {1-[7-chloro-thieno[3,2-b]pyridine-2-carbonyl]-pyrrolidin-3-yl}-amide The title compound was prepared from methanesulfonyl chloride and (3-amino-pyrrolidin-1-yl)-(7-chloro-thieno[3,2-b]pyridin-2yl)-methanone by a procedure analogous to Example 64C. MS: 360/362 (MH+); HPLC Rf: 3.22 min.; HPLC purity 98%.

B. (+/−)-Methanesulfonic acid {1-[7-(2-methyl-1H-indol-5-ylamino)-thieno[3,2-b]pyridine-2-carbonyl]-pyrrolidin-3-yl}-amide The title compound was prepared from (+/−)-methanesulfonic acid {1-[7-chloro-thieno[3,2-b]pyridine-2-carbonyl]-pyrrolidin-3-yl}-amide and 2-methyl-1H-indol-5-ylamine by a procedure analogous to Example 1C. MS: 470 (MH+); HPLC Rf: 3.23 min.; HPLC purity 93%.

EXAMPLE 73

A. (+/−)-Cyclobutane carboxylic acid methyl-{1-[7-chloro-thieno[3,2-b]pyridine-2-carbonyl]-pyrrolidin-3-yl}-amide The title compound was prepared from cyclobutane carbonyl chloride and (3-methylamino-pyrrolidin-1-yl)-(7-chloro-thieno[3,2-b]pyridin-2yl)-methanone by a procedure analogous to Example 64C. MS: 378/380 (MH+); HPLC Rf: 4.71 min.; HPLC purity 98%.

B. (+/−)-Cyclobutane carboxylic acid methyl-{1-[7-(2-methyl-1H-indol-5-ylamino)-thieno[3,2-b]pyridine-2-carbonyl]-pyrrolidin-3-yl}-amide The title compound was prepared from (+/−)-cyclobutane carboxylic acid methyl-{1-[7-chloro-thieno[3,2-b]pyridine-2-carbonyl]-pyrrolidin-3-yl}-amide and 2-methyl-1H-indol-5-ylamine by a procedure analogous to Example 1C. MS: 488 (MH+); HPLC Rf: 4.84 min.; HPLC purity 95%.

EXAMPLE 74

A. (+/−)-Dimethylsulfamic acid methyl-{1-[7-chloro-thieno[3,2-b]pyridine-2-carbonyl]-pyrrolidin-3-yl}-amide The title compound was prepared from dimethylsulfamoyl chloride and (3-methylamino-pyrrolidin-1-yl)-(7-chloro-thieno[3,2-b]pyridin-2yl)-methanone by a procedure analogous to Example 64C. MS: 403/405 (MH+); HPLC Rf: 4.76 min.; HPLC purity 98%.

B. (+/−)-Dimethylsulfamic acid methyl{1-[7-(2-methyl-1H-indol-5-ylamino)-thieno[3,2-b]pyridine-2-carbonyl]-pyrrolidin-3-yl}-amide The title compound was prepared from (+/−)-dimethylsulfamic acid methyl-{1-[7-chloro-thieno[3,2-b]pyridine-2-carbonyl]-pyrrolidin-3-yl}-amide and 2-methyl-1H-indol-5-ylamine by a procedure analogous to Example 1C. MS: 513 (MH+); HPLC Rf: 4.76 min.; HPLC purity 92%.

EXAMPLE 75

A. (+/−)-Methanesulfonic acid methyl-{1-[7-chloro-thieno[3,2-b]pyridine-2-carbonyl]-pyrrolidin-3-yl}-amide The title compound was prepared from methanesulfonyl chloride and (3-methylamino-pyrrolidin-1-yl)-(7-chloro-thieno[3,2-b]pyridin-2yl)-methanone by a procedure analogous to Example 64C. MS: 374/376 (MH+); HPLC Rf: 4.14 min.; HPLC purity 98%.

B. (+/−)-Methanesulfonic acid methyl-{1-[7-(2-methyl-1H-indol-5-ylamino)-thieno[3,2-b]pyridine-2-carbonyl]-pyrrolidin-3-yl}-amide The title compound was prepared from (+/−)-methanesulfonic acid methyl-{1-[7-chloro-thieno[3,2-b]pyridine-2-carbonyl]-pyrrolidin-3-yl}-amide and 2-methyl-1H-indol-5-ylamine by a procedure analogous to Example 1C. MS: 484 (MH+); HPLC Rf: 3.69 min.; HPLC purity 91%.

EXAMPLE 76

A. (+/−)-7-Chloro-thieno[3,2-b]pyridine-2-carbonyl)-pyrrolidin-3-yl]-propionamide The title compound was prepared from propionyl chloride and ((+/−)-3-amino-pyrrolidin-1-yl)-(7-chloro-thieno[3,2-b]pyridin-2yl)-methanone by a procedure analogous to Example 70A. MS: 340.0/338.0 (MH+); HPLC Rf: 3.675 min.; HPLC purity 98%.

B. (+/−)-{1-[7-(2-Methyl-1H-indol-5-ylamino)-thieno[3,2-b]pyridine-2-carbonyl]-pyrrolidin-3-yl}-propionamide The title compound was prepared from (+/−)-7-chloro-thieno[3,2-b]pyridine-2-carbonyl)-pyrrolidin-3-yl]-propionamide and 2-methyl-1H-indol-5-ylamine by a procedure analogous to Example 1C. MS: 448.1 (MH+); HPLC Rf: 3.18 min.; HPLC purity: 94%.

EXAMPLE 77

A. (3S)-(7-Chloro-thieno[3,2-b]pyridin-2-yl)-(3-ethoxy-pyrrolidin-1-yl)-methanone The title compound was prepared from iodoethane and (3S)-(3-hydroxy-pyrrolidin-1-yl)-[7-chloro-thieno[3,2-b]pyridin-2-yl]-methanone by a procedure analogous to Example 67B. MS: 311.2/313.2 (MH+); HPLC Rf: 4.692 min.; HPLC purity: 96%.

B. (3S)-3-Ethoxy-pyrrolidin-1-yl)-[7-(2-methyl-1H-indol-5-ylamino)-thieno[3,2-b]pyridin-2-yl]-methanone The title compound was prepared from (3S)-(7-chloro-thieno[3,2-b]pyridin-2-yl)-(3-ethoxy-pyrrolidin-1-yl)-methanone and 2-methyl-1H-indol-5-ylamine by a procedure analogous to Example 1C. MS: 421.3 (MH+); HPLC Rf: 4.786 min.; HPLC purity: 95%.

EXAMPLE 78

A. (3R)-(7-Chloro-thieno[3,2-b]pyridin-2-yl)-(3-ethoxy-pyrrolidin-1-yl)-methanone The title compound was prepared from iodoethane and (3R)-(3-hydroxy-pyrrolidin-1-yl)-[7-chloro-thieno[3,2-b]pyridin-2-yl]-methanone by a procedure analogous to Example 67B. MS: 311.2/313.2 (MH+); HPLC Rf: 4.697 min.; HPLC purity: 98%.

B. (3R)-3-Ethoxy-pyrrolidin-1-yl)-[7-(2-methyl-1H-indol-5-ylamino)-thieno[3,2-b]pyridin-2-yl]-methanone The title compound was prepared from (3R)-(7-chloro-thieno[3,2-b]pyridin-2-yl)-(3-ethoxy-pyrrolidin-1-yl)-methanone and 2-methyl-1H-indol-5-ylamine by a procedure analogous to Example 1C. MS: 421.3 (MH+); HPLC Rf: 4.79 min.; HPLC purity: 97%.

EXAMPLE 79

A. (3R)-(7-Chloro-thieno[3,2-b]pyridin-2-yl)-(3-cyclopropylmethoxy-pyrrolidin-1-yl)-methanone The title compound was prepared from bromomethyl-cyclopropane and (3R)-(3-hydroxy-pyrrolidin-1-yl)-[7-chloro-thieno[3,2-b]pyridin-2-yl]-methanone by a procedure analogous to Example 67B. MS: 337.2/339.2 (MH+); HPLC Rf: 5.232 min.; HPLC purity 85%.

B. (3R)-(3-Cyclopropylmethoxy-pyrrolidin-1-yl)-[7-(2-methyl-1H-indol-5-ylamino)-thieno[3,2-b]pyridin-2-yl]-methanone The title compound was prepared from (3R)-(7-chloro-thieno[3,2-b]pyridin-2-yl)-(3-cyclopropylmethoxy-pyrrolidin-1-yl)-methanone and 2-methyl-1H-indol-5-ylamine by a procedure analogous to Example 1C. MS: 447.2 (MH+); HPLC Rf: 5.341 min.; HPLC purity: 100%.

EXAMPLE 80

A. (3S)-(7-Chloro-thieno[3,2-b]pyridin-2-yl)-(3-cyclopropylmethoxy-pyrrolidin-1-yl)-methanone The title compound was prepared from bromomethyl-cyclopropane and (3S)-(3-hydroxy-pyrrolidin-1-yl)-[7-chloro-thieno[3,2-b]pyridin-2-yl]-methanone by a procedure analogous to Example 67B. MS: 337.2/339.2 (MH+); HPLC Rf: 5.232 min.; 85%.

B. (3S)-(3-Cyclopropylmethoxy-pyrrolidin-1-yl)-[7-(2-methyl-1H-indol-5-ylamino)-thieno[3,2-b]pyridin-2-yl]-methanone The title compound was prepared from (3S)-(7-chloro-thieno[3,2-b]pyridin-2-yl)-(3-cyclopropylmethoxy-pyrrolidin-1-yl)-methanone and 2-methyl-1H-indol-5-ylamine by a procedure analogous to Example 1C. MS: 447.2 (MH+); HPLC Rf: 5.341 min.; HPLC purity: 100%.

EXAMPLE 81

A. (3R)-(7-Chloro-thieno[3,2-b]pyridin-2-yl)-[3-(2-methoxy-ethoxy)-pyrrolidin-1-yl]-methanone The title compound was prepared from 1-bromo-2-methoxy-ethane and (3R)-(3-hydroxy-pyrrolidin-1-yl)-[7-chloro-thieno[3,2-b]pyridin-2-yl]-methanone by a procedure analogous to Example 67B. MS: 341.2/343.2 (MH+); HPLC Rf: 4.082 min.; HPLC purity: 96%.

B. (3R)-[3-(2-Methoxy-ethoxy)-pyrrolidin-1-yl]-[7-(2-methyl-1H-indol-5-ylamino)-thieno[3,2-b]pyridin-2-yl]-methanone The title compound was prepared from (3R)-(7-chloro-thieno[3,2-b]pyridin-2-yl)-[3-(2-methoxy-ethoxy)-pyrrolidin-1-yl]-methanone and 2-methyl-1H-indol-5-ylamine by a procedure analogous to Example 1C. MS: 451.3 (MH+); HPLC Rf: 4.385 min.; HPLC purity: 97%.

EXAMPLE 82

A. (3S)-(7-Chloro-thieno[3,2-b]pyridin-2-yl)-[3-(2-methoxy-ethoxy)-pyrrolidin-1-yl]-methanone The title compound was prepared from 1-bromo-2-methoxy-ethane and (3R)-(3-hydroxy-pyrrolidin-1-yl)-[7-chloro-thieno[3,2-b]pyridin-2-yl]-methanone by a procedure analogous to Example 67B. MS: 341.2/343.2 (MH+); HPLC Rf: 4.236 min.; HPLC purity: 77%.

B. (3S)-[3-(2-Methoxy-ethoxy)-pyrrolidin-1-yl]-[7-(2-methyl-1H-indol-5-ylamino)-thieno[3,2-b]pyridin-2-yl]-methanone The title compound was prepared from (3S)-(7-chloro-thieno[3,2-b]pyridin-2-yl)-[3-(2-methoxy-ethoxy)-pyrrolidin-1-yl]-methanone and 2-methyl-1H-indol-5-ylamine by a procedure analogous to Example 1C. MS: 451.2 (MH+); HPLC Rf: 4.357 min.; HPLC purity: 97%.

EXAMPLES 83–88

Compounds from examples 83–88 were synthesized by one of two methods. Method A is a two-step method analogous to that described in Example 1B/C. Method B involves the coupling of an amine to 7-(2-methyl-1H-indol-5-ylamino)-thieno[3,2-b]pyridine-2-carboxylic acid by a method analogous to Example 21B.

| Example Number | Compound Name | Method | MS (MH+) | HPLC purity | HPLC Rf (min) |
|---|---|---|---|---|---|
| 83 | (+/−)-7-(2-Methyl-1H-indol-5-ylamino)-thieno[3,2-b]pyridine-2-carboxylic acid (1-benzyl-pyrrolidin-3-yl)-methyl-amide | B | 496.2 | n.d. | n.d. |
| 84 | (2S)-[7-(2-Methyl-1H-indol-5-ylamino)-thieno[3,2-b]pyridin-2-yl]-(2-pyrrolidin-1-ylmethyl-pyrrolidin-1-yl)-methanone | B | 460.4 | 96 | 4.80 |
| 85 | (2S)-(2-Benzhydryl-pyrrolidin-1-yl)-[7-(2-methyl-1H-indol-5-ylamino)-thieno[3,2-b]pyridin-2-yl]-methanone | B | 543.4 | 96 | 6.86 |
| 86 | (2S)-[7-(2-Methyl-1H-indol-5-ylamino)-thieno[3,2-b]pyridin-2-yl]-(2-phenylaminomethyl-pyrrolidin-1-yl)-methanone | B | 482.2 | 98 | 5.78 |
| 87 | (3R,4R)-(3,4-Dihydroxy-pyrrolidin-1-yl)-[7-(2-methyl-1H-indol-5-ylamino)-thieno[3,2-b]pyridin-2-yl]-methanone | B | 409.2 | 97 | 3.42 |
| 88 | (3R,4R)-(3,4-Dihydroxy-pyrrolidin-1-yl)-[7-(2-methyl-1H-indol-5-ylamino)-thieno[3,2-b]pyridin-2-yl]-methanone | B | 409.2 | 97 | 3.41 |

EXAMPLE 89

A. (3S,4S)-(7-Chloro-thieno[3,2-b]pyridin-2-yl)-(3,4-dihydroxy-pyrrolidin-1-yl)-methanone The title compound was prepared from lithium 7-chloro-thieno[3,2-b]pyridine-2-carboxylate and (3S,4S)- pyrrolidine-3,4-diol by a procedure analogous to Example 1B. MS: 299.3/301.3 (MH+); HPLC Rf: 3.091 min.; HPLC purity: 99%.

B. (3S,4S)-(7-Chloro-thieno[3,2-b]pyridin-2-yl)-(3,4-dimethoxy-pyrrolidin-1-yl)-methanone NaH (254 mg, 6.37 mmol) was added to a solution of (3S,4S)-(7-chloro-thieno[3,2-b]pyridin-2-yl)-(3,4-dihydroxy-pyrrolidin-1-yl)-methanone (543 mg, 1.82 mmol) in DMF at 0° C. After 30 min., MeI (645 mg, 4.55 mmol) was added dropwise. The resulting solution was allowed to warm to room temperature and stir for 12 h. The reaction was treated with saturated KCN (aq) and saturated ammonium chloride (aq). The aqueous layer was extracted with EtOAc (2x) the combined organic layers were dried over magnesium sulfate. The resulting material was purified on silica gel by flash column chromatography eluting with $CH_2Cl_2$/MeOH (98/2) to afford the title compound as a white solid (220 mg, 37%). MS: 327.2/329.2 (MH+); HPLC Rf: 4.448 min.; HPLC purity: 99%.

C. (3S,4S)-(3,4-Dimethoxy-pyrrolidin-1-yl)-[7-(2-methyl-1H-indol-5-ylamino)-thieno[3,2-b]pyridin-2-yl]-methanone The title compound was prepared from (3S,4S)-(7-chloro-thieno[3,2-b]pyridin-2-yl)-(3,4-dimethoxy-pyrrolidin-1-yl)-methanone and 2-methyl-1H-indol-5-ylamine by a procedure analogous to Example 1C MS: 437.4 (MH+); HPLC Rf: 4.432 min.; HPLC purity: 98%.

EXAMPLE 90

(3R,4R)-(3,4-Dimethoxy-pyrrolidin-1-yl)-[7-(2-methyl-1H-indol-5-ylamino)-thieno[3,2-b]pyridin-2-yl]-methanone The title compound was prepared by a procedure analogous to Example 89 using (3R,4R)-pyrrolidine-3,4-diol as starting material. MS: 437.4 (MH+); HPLC Rf: 4.052 min.; HPLC purity: 98%.

EXAMPLE 91 meso-(3,4-Dimethoxy-pyrrolidin-1-yl)-[7-(2-methyl-1H-indol-5-ylamino)-thieno[3,2-b]pyridin-2-yl]-methanone The title compound was prepared by a procedure analogous to Example 89 using meso-pyrrolidine-3,4-diol as starting material. MS: 437.2 (MH+); HPLC Rf: 4.141 min.; HPLC purity: 97%.

EXAMPLE 92

A. (S)-2-(1-Hydroxy-1-methyl-ethyl)-pyrrolidine-1-carboxylic acid benzyl ester

Methylmagnesium bromide (3.8 mL, 3.80 mmol, 3.0 M in $Et_2O$) was added dropwise to a solution of (S)-Pyrrolidine-1,2-dicarboxylic acid 1-benzyl ester 2-methyl ester (1.0 g, 3.8 mmol) in THF at 0° C. After 3 h the reaction was quenched with saturated $NH_4Cl$ (aq), the aqueous layer was extracted with $Et_2O$ (3x). The combined organic extracts were dried over $Na_2SO_4$, and the resulting material was purified on silica gel by flash column chromatography $CH_2Cl_2$/MeOH (97/3) to afford the title compound as a white solid (727 mg, 72%). MS: 264.2 (MH+); HPLC Rf: n.d.; HPLC purity: n.d.

B. (S)-2-Pyrrolidin-2-yl-propan-2-ol

A mixture of (S)-2-(1-hydroxy-1-methyl-ethyl)-pyrrolidine-1-carboxylic acid benzyl ester (0.727 g, 2.76 mmol) and Pd/C (10%, 72 mg) in EtOH was shaken with $H_2$ in a Parr bottle under 50 psi. After 12 h the reaction mixture was filtered through celite. HCl (9 mmol, 1 N in $Et_2O$) was added to the filtrate, the filtrate was then concentrated to give a white solid (350 mg, 98%).

C. (2S)-[2-(1-Hydroxy-1-methyl-ethyl)-pyrrolidin-1-yl]-[7-(2-methyl-1H-indol-5-ylamino)-thieno[3,2-b]pyridin-2-yl]-methanone The title compound was prepared from 7-(2-methyl-1H-indol-5-ylamino)-thieno[3,2-b]pyridine-2-carboxylic acid and (S)-2-pyrrolidin-2-yl-propan-2-ol by a procedure analogous to Example 21B. MS: 435.3; HPLC Rf: 4.134 min.; HPLC purity 95%.

EXAMPLE 93

A. (6-Amino-3-aza-bicyclo[3.1.0]hex-3-yl)-(7-chloro-thieno[3,2-b]pyridin-2-yl)-methanone Trifluoroacetic acid (2 mL) was added to a suspension of {3-[7-chloro-thieno[3,2-b]pyridine-2-carbonyl]-3-aza-bicyclo[3.1.0]hex-6-yl}-carbamic acid tert-butyl ester (1.43 g, 3.63 mmol) in $CH_2Cl_2$. After 24 h the reaction mixture was concentrated, and the resulting oil was purified on silica gel by flash column chromatography $CH_2Cl_2$/MeOH (80/20) to afford the title compound as a white solid (1.27 g, 99%). MS: 294.2/296.2 (MH+); HPLC Rf: 3.085 min.; HPLC purity: 97%.

B. (7-Chloro-thieno[3,2-b]pyridin-2-yl)-(6-dimethylamino-3-aza-bicyclo[3.1.0]hex-3-yl)-methanone $NaBH_3CN$ (211 mg, 3.36 mmol) was added to a solution of (6-amino-3-aza-bicyclo[3.1.0]hex-3-yl)-(7-chloro-thieno[3,2-b]pyridin-2-yl)-methanone (250 mg, 0.85 mmol) and formaldehyde (1.14 mL, 17 mmol) in $CH_3CN$ at 0° C. After 30 min AcOH (0.5 mL) was added and the reaction mixture was allowed to warm to room temperature. After 1 h the reaction mixture was concentrated, and the resulting residue was dissolved in $H_2O$. The resulting aqueous layer was adjusted to pH 9 with 6N NaOH. The resulting solution was extracted with $CH_2Cl_2$ (2x) and the combined organic extracts were dried over $Na_2SO_4$, filtered, then concentrated. The resulting material was purified on silica gel by flash column chromatography $CH_2Cl_2$/MeOH (85/15) to afford the title compound as a white solid (44 mg, 16%). MS: 322.2/324.2 (MH+); HPLC Rf: 3.62 min.; HPLC purity 95%.

C. (6-Amino-3-aza-bicyclo[3.1.0]hex-3-yl)-[7-(2-methyl-1H-indol-5-ylamino)-thieno[3,2-b]pyridin-2-yl]-methanone The title compound was prepared from (7-chloro-thieno[3,2-b]pyridin-2-yl)-(6-dimethylamino-3-aza-bicyclo[3.1.0]hex-3-yl)-methanone and 2-methyl-1H-indol-5-ylamine by a procedure analogous to example 1C. MS: 432.2 (MH+); HPLC Rf: 4.346 min.; HPLC purity: 99%.

EXAMPLE 94

A. (S)-2-Morpholin-4-ylmethyl-pyrrolidine-1-carboxylic acid tert-butyl ester

Methanesulfonyl chloride (1.7 g, 14.9 mmol) was added dropwise to a solution of (S)-2-hydroxymethyl-pyrrolidine-1-carboxylic acid tert-butyl ester (1.5 g, 7.45 mmol) and triethylamine (753 mg mg, 7.45 mmol) in $CH_2Cl_2$ at 0° C. After 3 h reaction mixture was concentrated to give a white solid. The resulting solid was suspended in toluene, morpholine (1.3 g, 14.9 mmol) was added, and the resulting mixture was heated to 110° C. in a sealed tube. After 12 h the reaction mixture was concentrated, the resulting residue was dissolved in EtOAc and water, the layers were separated, and the aqueous was further extracted with EtOAc. The combined organic extracts were dried over $Na_2SO_4$, and the material was purified on silica gel by flash column chromatography $CH_2Cl_2$/MeOH/$NH_4OH$ (98.5/1/0.5) to afford the title compound as a white solid (800 mg, 40%). MS: 271.2 (MH+); HPLC Rf: n.d.; HPLC purity: n.d.

B. (S)-4-Pyrrolidin-2-ylmethyl-morpholine

HCl (g) was introduced into a solution of (S)-2-morpholin-4-ylmethyl-pyrrolidine-1-carboxylic acid tert-butyl ester (400 mg, 1.47 mmol) in MeOH. After 5 min., the reaction solution was concentrated under reduced pressure to give a white solid (300 mg, 99%). MS: 170.9 (MH+); HPLC Rf: n.d.; HPLC purity: n.d.

C. (2S)-[7-(2-Methyl-1H-indol-5-ylamino)-thieno[3,2-b]pyridin-2-yl]-(2-morpholin-4-ylmethyl-pyrrolidin-1-yl)-methanone The title compound was prepared from (S)-4-pyrrolidin-2-ylmethyl-morpholine and 7-(2-methyl-1H-indol-5-ylamino)-thieno[3,2-b]pyridine-2-carboxylic acid by a procedure analogous to Example 21B. MS: 476.3 (MH+); HPLC Rf: 5.378 min.; HPLC purity: 92%.

Compounds from examples 95–98 were synthesized by a procedure analogous to Example 94.

| Example Number | Compound Name | MS (MH+) | HPLC purity | HPLC Rf (min) |
|---|---|---|---|---|
| 95 | (2R)-[7-(2-Methyl-1H-indol-5-ylamino)-thieno[3,2-b]pyridin-2-yl]-(2-morpholin-4-ylmethyl-pyrrolidin-1-yl)-methanone | 476.1 | 92 | 5.52 |
| 96 | (2S)-(2-Dimethylaminomethyl-pyrrolidin-1-yl)-[7-(2-methyl-1H-indol-5-ylamino)-thieno[3,2-b]pyridin-2-yl]-methanone | 434.2 | 98 | 4.63 |
| 97 | (2)-(2-Dimethylaminomethyl-pyrrolidin-1-yl)-[7-(2-methyl-1H-indol-5-ylamino)-thieno[3,2-b]pyridin-2-yl]-methanone | 434.4 | 98 | 4.65 |
| 98 | (2R)-[7-(2-Methyl-1H-indol-5-ylamino)-thieno[3,2-b]pyridin-2-yl]-(2-pyrrolidin-1-ylmethyl-pyrrolidin-1-yl)-methanone | 460.1 | n.d. | n.d. |

EXAMPLE 99

(3R)-[7-(2,3-Dimethyl-1H-indol-5-ylamino)-thieno[3,2-b]pyridin-2-yl]-(3-methoxy-pyrrolidin-1-yl)-methanone A solution of (3R)-(7-chloro-thieno[3,2-b]pyridin-2-yl)-(3-methoxy-pyrrolidin-1-yl)-methanone (139 mg, 0.47 mmol) and 2,3-dimethyl-1H-indol-5-ylamine (75 mg, 0.47 mmol) in EtOH (10 mL) was heated to reflux. After 12 h the reaction mixture was concentrated onto silica gel (5 mL) and purified on silica gel by flash column chromatography $CH_2Cl_2$/MeOH/$NH_4OH$ (98.5/1/0.5) to afford the title compound as a yellow solid, (190 mg). MS: 421.3 (MH+); HPLC Rf: 4.708 min.; HPLC purity: 99%.

EXAMPLE 100

(3S)-[7-(2,3-Dimethyl-1H-indol-5-ylamino)-thieno[3,2-b]pyridin-2-yl]-(3-methoxy-pyrrolidin-1-yl)-methanone The title compound was prepared from (3S)-(7-chloro-thieno[3,2-b]pyridin-2-yl)-(3-methoxy-pyrrolidin-1-yl)-methanone and 2,3-dimethyl-1H-indol-5-ylamine by a procedure analogous to Example 99. MS: 421.2 (MH+); HPLC Rf: 4.80 min.; HPLC purity: 99%.

EXAMPLES 101–102

Compounds from examples 101–102 were synthesized by a procedure analogous to that described in Example 1B/99A.

| Example Number | Compound Name | MS (MH+) | HPLC purity | HPLC Rf (min) |
|---|---|---|---|---|
| 101 | (2R)-[7-(2,3-Dimethyl-1H-indol-5-ylamino)-thieno[3,2-b]pyridin-2-yl]-(2-methoxymethyl-pyrrolidin-1-yl)-methanone | 35 | 6% | .11 |
| 102 | (2S)-[7-(2,3-Dimethyl-1H-indol-5-ylamino)-thieno[3,2-b]pyridin-2-yl]-(2-methoxymethyl-pyrrolidin-1-yl)-methanone | 35 | 7% | .10 |

EXAMPLE 103

(3R)-[7-(3-Chloro-2-methyl-1H-indol-5-ylamino)-thieno[3,2-b]pyridin-2-yl]-(3-methoxy-pyrrolidin-1-yl)-methanone A solution of (3R)-(7-chloro-thieno[3,2-b]pyridin-2-yl)-(3-methoxy-pyrrolidin-1-yl)-methanone (75 mg, 0.25 mmol) and 3-chloro-2-methyl-1H-indol-5-ylamine (45 mg, 0.25 mmol) in EtOH (10 mL) was heated to reflux. After 48 h the reaction mixture was concentrated onto silica gel (5 mL) and purified on silica gel by flash column chromatography $CH_2Cl_2$/MeOH/$NH_4OH$ (95/41) to afford the title compound as a yellow solid, (94 mg). MS: 441.2/443.2, 407.2 (MH+); HPLC Rf: 4.93 min.; HPLC purity: 98%.

EXAMPLE 104

(3S)-[7-(3-Chloro-2-methyl-1H-indol-5-ylamino)-thieno[3,2-b]pyridin-2-yl]-(3-methoxy-pyrrolidin-1-yl)-methanone The title compound was prepared from (3S)-(7-chloro-thieno[3,2-b]pyridin-2-yl)-(3-methoxy-pyrrolidin-1-yl)-methanone and 3-chloro-2-methyl-1H-indol-5-ylamine by a procedure analogous to Example 103. MS: 441.2/443.2; 407.2(MH+); HPLC Rf: 4.96 min.; HPLC purity: 98%.

EXAMPLES 105–106

Compounds from examples 105–106 were synthesized by a procedure analogous to that described in Examples 1B/103A.

| 105 | (2R)-[7-(3-Chloro-2-methyl-1H-indol-5-ylamino)-thieno[3,2-b]pyridin-2-yl]-(2-methoxymethyl-pyrrolidin-1-yl)-methanone | 457 | 99% | 5.37 |
|---|---|---|---|---|
| 106 | (2S)-[7-(3-Chloro-2-methyl-1H-indol-5-ylamino)-thieno[3,2-b]pyridin-2-yl]-(2-methoxymethyl-pyrrolidin-1-yl)-methanone | 457 | 98% | 5.37 |

EXAMPLE 107

A. 1-(1-Benzhydryl-azetidin-3-yl)-pyrrolidine

Pyrrolidine (142 mg, 2 mmol) and triethylamine (100 mg, 1 mmol) were added to a solution of methanesulfonic acid 1-benzhydryl-azetidin-3-yl ester (317.4 mg, 1 mmol) in DMF (6 mL). (The methanesulfonic acid 1-benzhydryl-azetidin-3-yl ester was prepared as described in J. Org. Chem. 1991, 56, 6729–6730). The reaction mixture was heated at 70° C. overnight. After cooling to room temperature, the reaction mixture was treated with water. The aqueous layer was extracted with EtOAc (3×15 mL). The combined organic extracts were washed with brine and dried over sodium sulfate. The solvent was then removed under reduced pressure. Purification by flash chromatography on silica gel ($CH_2Cl_2$/MeOH 96:4) afforded the title compound as an oil (184 mg, 65%). MS: 293 (MH+); HPLC Rf: 5.95 min; HPLC purity: 92%.

B. 1-Azetidin-3-yl-pyrrolidine

HCl (gas) was bubbled through a solution of 1-(1-benzhydryl-azetidin-3-yl)-pyrrolidine (184 mg, 0.63 mmol) in MeOH (10 mL). After 15 min, TLC showed the reaction to be complete. The resulting HCl salt was obtained as a light yellow solid after removal of the solvent. The HCl salt was then re-dissolved in MeOH and exposed to hydrogen in presence of $Pd(OH)_2$ (53 mg) for 4 hours. The $Pd(OH)_2$ was removed by filtration through Celite and was washed with MeOH. The titled compound was afforded as a light yellow solid (105 mg, 92%) after concentrating the filtrate under reduced pressure. MS: 363 (MH+)

C. [7-(2-Methyl-1H-indol-5-ylamino)-thieno[3,2-b]pyridin-2-yl]-(3-pyrrolidin-1-yl-azetidin-1-yl)-methanone The title compound was prepared from 1-azetidin-3-yl-pyrrolidine and 7-(2-methyl-1H-indol-5-ylamino)-thieno[3,2-b]pyridine-2-carboxylic acid by a procedure analogous to Example 21B. MS: 312 (MH+); HPLC Rf: 3.211 min; HPLC purity: 96%.

EXAMPLE 108–110

Compounds from examples 108–110 were synthesized by the same method described for Example 107.

| Example Number | Compound Name | MS (MH+) | HPLC purity | HPLC Rf (min) |
|---|---|---|---|---|
| 108 | (3-Dimethylamino-azetidin-1-yl)-[7-(2-methyl-1H-indol-5-ylamino)-thieno[3,2-b]pyridin-2-yl]-methanone | 406 | 96% | 3.22 |
| 109 | (3-Diethylamino-azetidin-1-yl)-[7-(2-methyl-1H-indol-5-ylamino)-thieno[3,2-b]pyridin-2-yl]-methanone | 434 | 94% | 4.30 |

| Example Number | Compound Name | MS (MH+) | HPLC purity | HPLC Rf (min) |
|---|---|---|---|---|
| 110 | [7-(2-Methyl-1H-indol-5-ylamino)-thieno[3,2-b]pyridin-2-yl]-(3-morpholin-4-yl-azetidin-1-yl)-methanone | 448 | 97% | 4.09 |

EXAMPLE 111

A. 4-(7-Chloro-thieno[3,2-b]pyridine-2-carbonyl)-piperazine-1-carboxylic acid tert-butyl ester The title compound was prepared from lithium 7-chloro-thieno[3,2-b]pyridine-2-carboxylate and piperazine-1-carboxylic acid tert-butyl ester by a procedure analogous to Example 1B. MS: 383 (MH+); HPLC Rf: 5.69; HPLC purity: 99%.

B. 1-[4-(7-Chloro-thieno[3,2-b]pyridine-2-carbonyl)-piperazin-1-yl]-ethanone

HCl (gas) was bubbled through a solution of 4-(7-chloro-thieno[3,2-b]pyridine-2-carbonyl)-piperazine-1-carboxylic acid tert-butyl ester (270 mg, 0.71 mmol) in MeOH (5 mL). After 15 min, TLC showed the reaction to be complete. The resulting HCl salt was obtained as a yellow oil (199 mg, 99%) after the solvent was removed under pressure. The title compound was prepared from the resulting HCl salt and acetyl chloride by a procedure analogous to Example 70A. MS: 325 (MH+); HPLC Rf: 3.62; HPLC purity: 95%.

C. 1-{4-[7-(2-Methyl-1H-indol-5-ylamino)-thieno[3,2-b]pyridine-2-carbonyl]-piperazin-1-yl}-ethanone The title compound was prepared from 1-[4-(7-chloro-thieno[3,2-b]pyridine-2-carbonyl)-piperazin-1-yl]-ethanone and 2-methyl-1H-indol-5-ylamine by a procedure analogous to Example 1C. MS: 434 (MH+); HPLC Rf: 3.52; HPLC purity: 99%.

EXAMPLES 112–113

Compounds from examples 112–113 were synthesized by the same method as described for Example 111. In each case, 4-(7-chloro-thieno[3,2-b]pyridine-2-carbonyl)-piperazine-1-carboxylic acid tert-butyl ester was treated with HCl (gas). The resulting HCl salt was treated with a commercially available sulfonyl chloride by a procedure analogous to Example 64B to give the corresponding sulfonamide. The sulfonamides were then coupled with 2-methyl-1H-indole-5-ylamine according to Example 1C to give the title compounds.

EXAMPLE 114

A. 1-Benzhydryl-azetidin-3-ylamine

Ammonia gas was bubbled through a solution of methanesulfonic acid 1-benzhydryl-azetidin-3-yl ester (952.4 mg, 3 mmol) in MeOH (15 mL). After 2 hours, TLC showed the reaction to be complete. The title compound was obtained as a white solid (643.5 mg, 90%) after removal of the solvent. MS: 239 (MH+); HPLC Rf: 3.54 min; HPLC purity: 98%.

B. N-(1-Benzhydryl-azetidin-3-yl)-acetamide

The title compound was prepared from 1-benzhydryl-azetidin-3-ylamine and acetyl chloride by a procedure analogous to Example 70A. MS: 281 (MH+); HPLC Rf: 5.57 min; HPLC purity: 93%.

C. N-Azetidin-3-yl-acetamide

The title compound was prepared by a method analogous to Example 70A. MS: 115 (MH+).

D. N-{1-[7-(2-Methyl-1H-indol-5-ylamino)-thieno[3,2-b]pyridine-2-carbonyl]-azetidin-3-yl}-acetamide The title compound was prepared by a method analogous to Example 21B. MS: 421 (MH+); HPLC Rf: 4.43 min; HPLC purity: 95%.

EXAMPLE 115

A. (7-Chloro-thieno[3,2-b]pyridin-2-yl)-(2R)-(2-ethoxymethyl-pyrrolidin-1-yl)-methanone NaH (80 mg, 2 mmol) was added to a solution of (2R)-(2-hydroxymethyl-pyrrolidin-1-yl)-[7-chloro-thieno[3,2-b]pyridin-2-yl]-methanone (297 mg, 1 mmol) in DMF (5 mL), at 0° C. The reaction mixture was allowed to stir for 20 min, and EtI (234 mg, 1.5 mmol) was added dropwise. After 3 h the reaction was quenched with saturated aqueous KCN (10 mL). The aqueous layer was extracted with CH$_2$Cl$_2$ (3×15 mL). The combined organic extracts were dried (Na$_2$SO$_4$), and the solvent was removed. Purification by flash chromatography on silica gel (CH$_2$Cl$_2$/MeOH 94:6) afforded the title compound as a white solid (145 mg, 50%). MS: 326 (MH+); HPLC Rf: 5.11 min; HPLC purity: 97%.

B. (2R)-(2-Ethoxymethyl-pyrrolidin-1-yl)-[7-(2-methyl-1H-indol-5-ylamino)-thieno[3,2-b]pyridin-2-yl]-methanone

| Example Number | Compound Name | MS (MH+) | HPLC purity | HPLC Rf (min) |
|---|---|---|---|---|
| 112 | (4-Methanesulfonyl-piperazin-1-yl)-[7-(2-methyl-1H-indol-5-ylamino)-thieno[3,2-b]pyridin-2-yl]-methanone | 470 | 98% | 4.26 |
| 113 | 4-[7-(2-Methyl-1H-indol-5-ylamino)-thieno[3,2-b]pyridine-2-carbonyl]-piperazine-1-sulfonic acid dimethylamide | 499 | 94% | 4.76 |

A solution of (7-chloro-thieno[3,2-b]pyridin-2-yl)-pyrrolidin-1-yl-methanone (130 mg, 0.4 mmol) and 2-methyl-1H-indol-5-ylamine (70 mg, 0.48 mmol) in EtOH (5 mL) was heated to reflux for 48 h. The reaction mixture was cooled to room temperature and concentrated onto silica gel. Purification by flash chromatography on silica gel eluting with CH$_2$Cl$_2$/MeOH/NEt$_3$ (94.5/5/0.5) afforded the title compound as a yellow solid (150 mg, 86%). MS: 435 (MH+); HPLC Rf: 5.37 min; HPLC purity: 98%.

EXAMPLES 116–122

Compounds from examples 116–122 were synthesized by the same method described for Example 115. In each case, a commercially available alkyl iodide was coupled with of 3R or 3S-(3-hydroxy-pyrrolidin-1-yl)-[7-chloro-thieno[3,2-b]pyridin-2-yl]-methanone by a procedure analogous to Example 115, and the resulting thienopyridine chloride were treated with 2-methyl-1H-indole-5-ylamine according to Example 1C to give the title compounds.

| Example Number | Compound Name | MS (MH+) | HPLC purity | HPLC Rf (min) |
|---|---|---|---|---|
| 116 | (2R)-(2-Isopropoxymethyl-pyrrolidin-1-yl)-[7-(2-methyl-1H-indol-5-ylamino)-thieno[3,2-b]pyridin-2-yl]-methanone | 449 | 95% | 6.14 |
| 117 | (2S)-(2-Cyclopropylmethoxymethyl-pyrrolidin-1-yl)-[7-(2-methyl-1H-indol-5-ylamino)-thieno[3,2-b]pyridin-2-yl]-methanone | 461 | 97% | 5.68 |
| 118 | (2R)-(2-Cyclopropylmethoxymethyl-pyrrolidin-1-yl)-[7-(2-methyl-1H-indol-5-ylamino)-thieno[3,2-b]pyridin-2-yl]-methanone | 461 | 97% | 5.69 |
| 119 | [2-(2R)-(2-Methoxy-ethoxymethyl)-pyrrolidin-1-yl]-[7-(2-methyl-1H-indol-5-ylamino)-thieno[3,2-b]pyridin-2-yl]-methanone | 466 | 96% | 4.78 |
| 120 | (2S)-(2-Ethoxymethyl-pyrrolidin-1-yl)-[7-(2-methyl-1H-indol-5-ylamino)-thieno[3,2-b]pyridin-2-yl]-methanone | 435 | 96% | 5.10 |
| 121 | [2-(2S)-(2-Methoxy-ethoxymethyl)-pyrrolidin-1-yl]-[7-(2-methyl-1H-indol-5-ylamino)-thieno[3,2-b]pyridin-2-yl]-methanone | 466 | 96% | 4.58 |
| 122 | (2S)-(2-Isopropoxymethyl-pyrrolidin-1-yl)-[7-(2-methyl-1H-indol-5-ylamino)-thieno[3,2-b]pyridin-2-yl]-methanone | 450 | 95% | 5.24 |

EXAMPLE 123

A. (2S)-(7-Chloro-thieno[3,2-b]pyridin-2-yl)-(2-methoxymethyl-pyrrolidin-1-yl)-methanone This compound was prepared as described for Example 1B, using (2S)-2-methoxymethylpyrrolidine as starting material.

B. (2S)-(2-Methoxymethyl-pyrrolidin-1-yl)-[7-(2-methyl-quinolin-6ylamino)-thieno[3,2-b]pyridin-2-yl]-methanone Cesium Carbonate (117 mg, 0.36 mmol) was added to a solution of (7-chloro-thieno[3,2-b]pyridin-2-yl)-(2-hydroxymethyl-pyrrolidin-1-yl)-methanone 1(56 mg, 0.18 mmol) in DMF (4 mL). The reaction mixture was heated to 85° C. for 1.5 hours with stirring. After cooling to room temperature, 2-methyl-quinolin-6-ylamine (57 mg, 0.36 mmol) was added to the reaction mixture, and the resulting mixture was heated to 90° C. for 48 hours. The reaction mixture was treated with water and extracted with EtOAc (3×15 mL). The combined organic extracts were was dried over sodium sulfate, and the solvent was removed under reduced pressure. Purification by flash chromatography on silica gel with CH$_2$Cl$_2$/MeOH (95/5) afforded the title compound as a white solid. MS: 435 (MH+); HPLC Rf: 5.35 min; HPLC purity: 97%.

EXAMPLE 124

(2R)-(2-Methoxymethyl-pyrrolidin-1-yl)-[7-(2-methyl-quinolin-6-ylamino)-thieno[3,2-b]pyridin-2-yl]-methanone The title compound was prepared by method analogous to Example 123, using (2R)-2-methoxymethyl-pyrrolidine as a starting material. MS: 435 (MH+); HPLC Rf: 5.34 min; HPLC purity: 98%.

EXAMPLE 125

A. (2R)-(2-Methoxymethyl-pyrrolidin-1-yl)-[7-(2-methyl-1H-indol-5-ylamino)-thieno[3,2-b]pyridin-2-yl]-methanone This compound was prepared by method analogous to Example 1, using (2R)-2-methoxymethyl-pyrrolidine as a starting material.

B. N-(1-Acetyl-2-methyl-1H-indol-5-yl)-N-[2-(2R)-(2-methoxymethyl-pyrrolidine-1-carbonyl)-thieno[3,2-b]pyridin-7-yl]-acetamide The title compound was prepared by method analogous to Example 70A using (2R)-(2-methoxymethyl-pyrrolidin-1-yl)-[7-(2-methyl-1H-indol-5-ylamino)-thieno[3,2-b]pyridin-2-yl]-methanone and acetyl chloride as starting materials. MS: 505 (MH+); HPLC Rf: 4.11 min; HPLC purity: 99%.

EXAMPLE 126

A. (2R)-(2-Methoxymethyl-pyrrolidin-1-yl)-[7-(2-methyl-1H-indol-5-ylamino)-thieno[3,2-b]pyridin-2-yl]-methanone This compound was prepared by method analogous to Example 1, using enantiomerically pure (2R)-2-methoxymethyl-pyrrolidine as a starting material.

B. 1-{5-[2-(2R)-(2-Methoxymethyl-pyrrolidine-1-carbonyl)-thieno[3,2-b]pyridin-7-ylamino]-2-methyl-indol-1-yl}-ethanone The title compound was prepared by method analogous to Example 70A using (2R)-(2-methoxymethyl-pyrrolidin-1-yl)-[7-(2-methyl-1H-indol-5-ylamino)-thieno[3,2-b]pyridin-2-yl]-methanone and acetyl chloride as starting materials. MS: 463 (MH+); HPLC Rf: 4.88 min; HPLC purity: 94%.

EXAMPLE 127

A. (2R)-(2-Methoxymethyl-pyrrolidin-1-yl)-[7-(2-methyl-1H-indol-5-ylamino)-thieno[3,2-b]pyridin-2-yl]-methanone This compound was prepared by method analogous to Example 1, using enantiomerically pure (2R)-2-methoxymethyl-pyrrolidine as a starting material.

B. {7-[Ethyl-(1-ethyl-2-methyl-1H-indol-5-yl)-amino]-thieno[3,2-b] pyridin-2-yl}-(2R)-2-methoxymethyl-pyrrolidin-1-yl)-methanone The title compound was prepared from (2R)-2-methoxymethyl-pyrrolidin-1-yl)-[7-(2-methyl-1H-indol-5-ylamino)-thieno[3,2-b]pyridin-2-yl]-methanone and EtI by a procedure analogous to Example 115A. MS: 449 (MH+); HPLC Rf: 5.53 min; HPLC purity: 95%.

EXAMPLE 128

{7-[(1,2-Dimethyl-1H-indol-5-yl)-methyl-amino]-thieno[3,2-b]pyridin-2-yl}-(2R)-(2-methoxymethyl-pyrrolidin-1-yl)-methanone The title compound was prepared by method analogous to Example 127, using MeI as the alkylating agent. MS: 435 (MH+); HPLC Rf: 5.38 min; HPLC purity: 97%.

EXAMPLE 129

A. (R)-2-(1-Benzyl-pyrrolidin-2-yl)-propan-2-ol

The title compound was prepared from (R)-1-benzyl-pyrrolidine-2-carboxylic acid ethyl ester by a procedure analogous to Example 92A. MS: 220.2 (MH+); HPLC Rf: 2.247 min.; HPLC purity: 80%.

B. (R)-2-Pyrrolidin-2-yl-propan-2-ol

A mixture of (R)-2-(1-benzyl-pyrrolidin-2-yl)-propan-2-ol (582 mg, 2.65 mmol), HOAc (3 mL), and Pd(OH)$_2$/C (200 mg) in MeOH was shaken in a Parr bottle with H$_2$ under 50 psi for 24 h. The reaction mixture was then filtered through celite eluting with MeOH. HCl (g) was passed through the filtrate, and the filtrate was then concentrated to afford the title compound as a gray solid (419 mg, 95%). MS: 130.1 (MH+); HPLC Rf: n.d.; HPLC purity: n.d.

C. (2R)-[2-(1-Hydroxy-1-methyl-ethyl)-pyrrolidin-1-yl]-[7-(2-methyl-1H-indol-5-ylamino)-thieno[3,2-b]pyridin-2-yl]-methanone The title compound was prepared from 7-(2-methyl-1H-indol-5-ylamino)-thieno[3,2-b]pyridine-2-carboxylic acid and (R)-2-pyrrolidin-2-yl-propan-2-ol by a procedure analogous to Example 21B. MS: 435.2; HPLC Rf: 4.656 min.; HPLC purity: 97%.

What is claimed:

1. A compound of the formula of formula 1

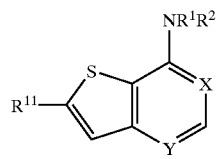

or a pharmaceutically acceptable salt, or hydrate thereof,

X is CH;

Y is N;

$R^1$ is H or $C_1$–$C_6$ alkyl;

$R^2$ is a group of the formula

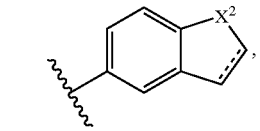

2

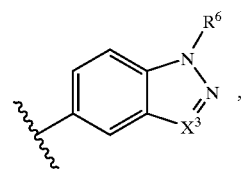

3

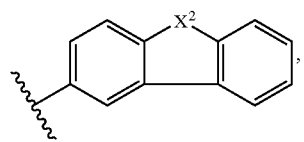

4

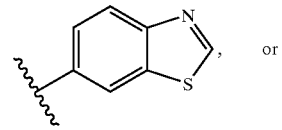

5 or

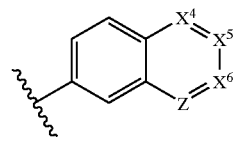

6 wherein $X^2$ is —S—, —N($R^6$)— or O, and $X^3$, $X^4$, $X^5$, $X^6$, and Z is N or CH, the dashed line in formula 2 represents an optional double bond, and the above $R^2$ groups of formulas 2, 4 and 6 are optionally substituted by 1 to 5 $R^5$ substituents and the $R^2$ groups of formulas 3 and 5 are optionally substituted by 1 to 3 $R^5$ substituents;

each $R^5$ is independently selected from halo, cyano, trifluoromethoxy, trifluoromethyl, —C(O)$R^8$, —N$R^6$C(O)$R^7$, —C(O)N$R^6R^7$, —N$R^6R^7$, —O$R^9$, —SO$_2$N$R^6R^7$, —SO$_2R^6$, —N$R^6$SO$_2R^7$, $C_1$–$C_6$ alkyl, $C_2$–$C_6$ alkenyl, $C_2$–$C_6$ alkynyl, —(CH$_2$)$_j$O(CH$_2$)$_q$N$R^6R^7$, —(CH$_2$)$_j$O(CH$_2$)$_q$O$R^9$, —(CH$_2$)$_j$O$R^9$, —S(O)$_j$(C$_1$–C$_6$ alkyl), —(CH$_2$)$_t$(C$_6$–C$_{10}$ aryl), —(CH$_2$)$_t$(5 to 10 membered heterocyclic), —(CH$_2$)$_t$O(CH$_2$)$_q$(5 to 10 membered heterocyclic), —C(O)(CH$_2$)$_t$(5 to 10 membered heterocyclic), —(CH$_2$)$_j$N$R^7$(CH$_2$)$_q$N$R^6R^7$, —(CH$_2$)$_j$N$R^7$CH$_2$C(O)N$R^6R^7$, —(CH$_2$)$_j$N$R^7$(CH$_2$)$_q$N$R^9$C(O)$R^8$, —(CH$_2$)$_j$N$R^7$(CH$_2$)$_t$O(CH$_2$)$_q$O$R^9$, —(CH$_2$)$_j$N$R^7$(CH$_2$)$_q$S(O)$_j$(C$_1$–C$_6$ alkyl), —(CH$_2$)$_j$N$R^7$(CH$_2$)$_t$$R^6$, —SO$_2$(CH$_2$)$_t$(C$_6$–C$_{10}$ aryl), and —SO$_2$(CH$_2$)$_t$(5 to 10 membered heterocyclic), wherein j is an integer from 0 to 2, t is an integer from 0 to 6, q is an integer from 2 to 6, the —(CH$_2$)$_q$— and —(CH$_2$)$_t$— moieties of the foregoing $R^5$ groups optionally include a carbon-carbon double or triple bond where t is an integer from 2 to 6, and the alkyl, aryl and heterocyclic moieties of the foregoing $R^5$ groups are optionally substituted by 1 to 3 substituents independently selected from halo, cyano, trifluoromethyl, —C(O)$R^8$, —N$R^6$C(O)$R^7$, —C(O)N$R^6R^7$, —(CH$_2$)$_t$N$R^6R^7$, —SO$_2R^6$, —SO$_2$N$R^6R^7$, $C_1$–$C_6$ alkyl, —(CH$_2$)$_t$(5 to 10 membered heterocyclic), —(CH$_2$)$_t$O(CH$_2$)$_q$O$R^9$, and —(CH$_2$)$_t$OR$^9$, wherein t is an integer from 0 to 6 and q is an integer from 2 to 6;

each R$^6$ and R$^7$ is independently selected from H, C$_1$–C$_6$ alkyl, —(CH$_2$)$_t$(C$_6$–C$_{10}$ aryl), —(CH$_2$)$_t$(5 to 10 membered heterocyclic), —(CH$_2$)$_t$O(CH$_2$)$_q$OR$^9$, and —(CH$_2$)$_t$OR$^9$, wherein t is an integer from 0 to 6 and q is an integer from 2 to 6, and the alkyl, aryl and heterocyclic moieties of the foregoing R$^6$ and R$^7$ groups are optionally substituted by 1 to 3 substituents independently selected from halo, cyano, trifluoromethyl, —C(O)R$^8$, —NR$^9$C(O)R$^{10}$, —C(O)NR$^9$R$^{10}$, —NR$^9$R$^{10}$, C$_1$–C$_6$ alkyl, —(CH$_2$)$_t$(C$_6$–C$_{10}$ aryl), —(CH$_2$)$_t$(5 to 10 membered heterocyclic), —(CH$_2$)$_t$O(CH$_2$)$_q$OR$^9$, and —(CH$_2$)$_t$OR$^9$, wherein t is an integer from 0 to 6 and q is an integer from 2 to 6, with the proviso that where R$^6$ and R$^7$ are both attached to the same nitrogen, then R$^6$ and R$^7$ are not both bonded to the nitrogen directly through an oxygen;

each R$^8$ is independently selected from H, C$_1$–C$_{10}$ alkyl, —(CH$_2$)$_t$(C$_6$–C$_{10}$ aryl), and —(CH$_2$)$_t$(5 to 10 membered heterocyclic), wherein t is an integer from 0 to 6;

each R$^9$ and R$^{10}$ is independently selected from H and C$_1$–C$_6$ alkyl; and R$^{11}$ is —C(O)NR$^{12}$R$^{13}$, wherein R$^{12}$ and R$^{13}$ taken together with the nitrogen to which they are attached form a C$_5$–C$_9$ azabicyclic, aziridinyl, azetidinyl, pyrrolidinyl, piperidinyl, piperazinyl, or morpholinyl ring wherein said C$_5$–C$_9$ azabicyclic, aziridinyl, azetidinyl, pyrrolidinyl, piperidinyl, piperazinyl, or morpholinyl ring are optionally substituted by 1 to 5 R$^5$ substituents.

2. The compound of claim 1, wherein R$^{11}$ is —C(O)NR$^{12}$R$^{13}$ wherein R$^{12}$ and R$^{13}$ taken together with the nitrogen to which they are attached form a C$_5$–C$_9$ azabicyclic, aziridinyl, azetidinyl, or pyrrolidinyl ring wherein said C$_5$–C$_9$ azabicyclic, aziridinyl, azetidinyl, or pyrrolidinyl ring are optionally substituted by 1 to 5 R$^5$ substituents.

3. The compound of claim 2, wherein R$^{11}$ is —C(O)NR$^{12}$R$^{13}$ wherein R$^{12}$ and R$^{13}$ taken together with the nitrogen to which they are attached form a C$_5$–C$_9$ azabicyclic, azetidinyl or pyrrolidinyl ring wherein said C$_5$–C$_9$ azabicyclic, azetidinyl or pyrrolidinyl ring is optionally substituted by 1 to 5 R$^5$ substituents.

4. The compound of claim 3, wherein R$^{11}$ is —C(O)NR$^{12}$R$^{13}$ wherein R$^{12}$ and R$^{13}$ taken together with the nitrogen to which they are attached form a C$_5$–C$_9$ azabicyclic ring, wherein said C$_5$–C$_9$ azabicyclic ring is optionally substituted by 1 to 5 R$^5$ substituents.

5. The compound of claim 3, wherein R$^{11}$ is —C(O)NR$^{12}$R$^{13}$ wherein R$^{12}$ and R$^{13}$ taken together with the nitrogen to which they are attached to form an azetidinyl ring, wherein said azetidinyl ring is optionally substituted by 1 to 5 R$^5$ substituents.

6. The compound of claim 3, wherein R$^{11}$ is —C(O)NR$^{12}$R$^{13}$ wherein R$^{12}$ and R$^{13}$ taken together with the nitrogen to which they are attached to form a pyrrolidinyl ring, wherein said pyrrolidinyl ring is optionally substituted by 1 to 5 R$^5$ substituents.

7. The compound of claim 1, wherein said R$^2$ group is a group of formula 2 or 6, wherein said formulas 2 and 6 are optionally substituted by 1 to 5 R$^5$ substituents.

8. The compound of claim 1, wherein said compound is selected from the group consisting of:

Azetidin-1-yl-[7-(2-methyl-1H-indol-5-ylamino)-thieno[3,2-b]pyridin-2-yl]-methanone;

[7-(2-Methyl-1H-indol-5-ylamino)-thieno[3,2-b]pyridin-2-yl]-pyrrolidin-1-yl-methanone;

7-(2-Methyl-1H-indol-5-ylamino)-thieno[3,2-b]pyridine-2-carboxylic acid cyclohexyl-methyl-amide;

(2-Methoxymethyl-pyrrolidin-1-yl)-[7-(2-methyl-1H-indol-5-ylamino)-thieno[3,2-b]pyridin-2-yl]-methanone;

7-(2-Methyl-1H-indol-5-ylamino)-thieno[3,2-b]pyridine-2-carboxylic acid methyl-(2-morpholin-4-yl-ethyl)-amide;

N-{1-[7-(2-Methyl-1H-indol-5-ylamino)-thieno[3,2-b]pyridine-2-carbonyl]-pyrrolidin-3-yl}-acetamide;

N-Ethyl-N-{1-[7-(2-methyl-1H-indol-5-ylamino)-thieno[3,2-b]pyridine-2-carbonyl]-pyrrolidin-3-yl}-acetamide;

(3-Methylamino-pyrrolidin-1-yl)-[7-(2-methyl-1H-indol-5-ylamino)-thieno[3,2-b]pyridin-2-yl]-methanone;

(3-Dimethylamino-pyrrolidin-1-yl)-[7-(2-methyl-1H-indol-5-ylamino)-thieno[3,2-b]pyridin-2-yl]-methanone;

(6-Amino-3-aza-bicyclo[3.1.0]hex-3-yl)-[7-(2-methyl-1H-indol-5-ylamino)-thieno[3,2-b]pyridin-2-yl]-methanone;

(3-Dimethylamino-pyrrolidin-1-yl)-[7-(2-methyl-1H-indol-5-ylamino)-thieno[3,2-b]pyridin-2-yl]-methanone;

(2-Methoxymethyl-pyrrolidin-1-yl)-[7-(2-methyl-1H-indol-5-ylamino)-thieno[3,2-b]pyridin-2-yl]-methanone;

(3-Hydroxy-pyrrolidin-1-yl)-[7-(2-methyl-1H-indol-5-ylamino)-thieno[3,2-b]pyridin-2-yl]-methanone;

(2-Hydroxymethyl-pyrrolidin-1-yl)-[7-(2-methyl-1H-indol-5-ylamino)-thieno[3,2-b]pyridin-2-yl]-methanone;

(3-Methoxy-pyrrolidin-1-yl)-[7-(2-methyl-1H-indol-5-ylamino)-thieno[3,2-b]pyridin-2-yl]-methanone;

(3-Ethoxy-azetidin-1-yl)-[7-(2-methyl-1H-indol-5-ylamino)-thieno[3,2-b]pyridin-2-yl]-methanone;

N-Methyl-N-{1-[7-(2-methyl-1H-indol-5-ylamino)-thieno[3,2-b]pyridine-2-carbonyl]-pyrrolidin-3-yl}-acetamide;

cyclobutanecarboxylic acid {1-[7-(2-methyl-1H-indol-5-ylamino)-thieno[3,2-b]pyridine-2-carbonyl]-pyrrolidin-3-yl}-amide; pharmaceutically acceptable salts of said compounds; solvates of said compounds; and 9. The compound of claim 8, wherein said compound is selected from the group consisting of (2S)-(2-Methoxymethyl-pyrrolidin-1-yl)-[7-(2-methyl-1H-indol-5-ylamino)-thieno[3,2-b]pyridin-2-yl]-methanone;

(+/−)-N-Ethyl-N-{1-[7-(2-methyl-1H-indol-5-ylamino)-thieno[3,2-b]pyridine-2-carbonyl]-pyrrolidin-3-yl}-acetamide;

(3S)-(3-Dimethylamino-pyrrolidin-1-yl)-[7-(2-methyl-1H-indol-5-ylamino)-thieno[3,2-b]pyridin-2-yl]-methanone;

(+/−)-N-Methyl-N-{1-[7-(2-methyl-1H-indol-5-ylamino)-thieno[3,2-b]pyridine-2-carbonyl]-pyrrolidin-3-yl}-acetamide;

(2R)-(2-Methoxymethyl-pyrrolidin-1-yl)-[7-(2-methyl-1H-indol-5-ylamino)-thieno[3,2-b]pyridin-2-yl]-methanone;

(3S)-(3-Hydroxy-pyrrolidin-1-yl)-[7-(2-methyl-1H-indol-5-ylamino)-thieno[3,2-b]pyridin-2-yl]-methanone;

(3R)-(3-Hydroxy-pyrrolidin-1-yl)-[7-(2-methyl-1H-indol-5-ylamino)-thieno[3,2-b]pyridin-2-yl]-methanone;

(+/−)-Cyclobutanecarboxylic acid {1-[7-(2-methyl-1H-indol-5-ylamino)-thieno[3,2-b]pyridine-2-carbonyl]-pyrrolidin-3-yl}-amide;

6-Amino-3-aza-bicyclo[3.1.0]hex-3-yl)-[7-(2-methyl-1H-indol-5-ylamino)-thieno[3,2-b]pyridin-2-yl]-methanone;

(3S)-(3-Methoxy-pyrrolidin-1-yl)-[7-(2-methyl-1H-indol-5-ylamino)-thieno[3,2-b]pyridin-2-yl]-methanone; pharmaceutically acceptable salts of said compounds; solvates of said compounds.

10. A compound of claim 1, wherein $R^1$ is H; $R^2$ is

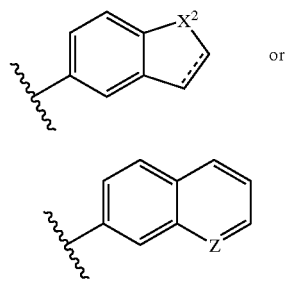

or

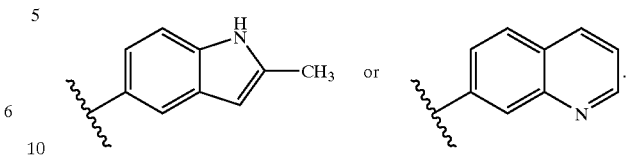

$X^2$ is —N($R^6$)—, the dashed line in formula 2 represents an optional double bond, Z is CH or N and the above $R^2$ group of formulas 2 and 6 are optionally substituted by 1 to 5 $R^5$.

11. The compound of claim 10, wherein $R^{11}$ is —C(O)N$R^{12}R^{13}$ wherein $R^{12}$ and $R^{13}$ taken together with the nitrogen to which they are attached form a $C_5$–$C_9$ azabicyclic, aziridinyl, azetidinyl, or pyrrolidinyl ring wherein said $C_5$–$C_9$ azabicyclic, aziridinyl, azetidinyl, or pyrrolidinyl ring is optionally substituted by 1 to 5 $R^5$ substituents.

12. The compound of claim 11, wherein $R^{11}$ is —C(O)N$R^{12}R^{13}$ wherein $R^{12}$ and $R^{13}$ taken together with the nitrogen to which they are attached form a $C_5$–$C_9$ azabicyclic, azetidinyl or pyrrolidinyl ring wherein said $C_5$–$C_9$ azabicyclic, azetidinyl or pyrrolidinyl ring is optionally substituted by 1 to 5 $R^5$ substituents.

13. The compound of claim 12, wherein $R^{11}$ is —C(O)N$R^{12}R^{13}$ wherein $R^{12}$ and $R^{13}$ taken together with the nitrogen to which they are attached form a $C_5$–$C_9$ azabicyclic ring wherein said $C_5$–$C_9$ azabicyclic ring is optionally substituted by 1 to 5 $R^5$ substituents.

14. The compound of claim 13, wherein $R^{11}$ is —C(O)N$R^{12}R^{13}$ wherein $R^{12}$ and $R^{13}$ taken together with the nitrogen to which they are attached form an azetidinyl ring wherein said azetidinyl ring is optionally substituted by 1 to 5 $R^5$ substituents.

15. The compound of claim 14, wherein $R^{11}$ is —C(O)N$R^{12}R^{13}$ wherein $R^{12}$ and $R^{13}$ taken together with the nitrogen to which they are attached form a pyrrolidinyl ring wherein said pyrrolidinyl ring is optionally substituted by 1 to 5 $R^5$ substituents.

16. A compound of claim 1, wherein $R^1$ is H; $R^2$ is

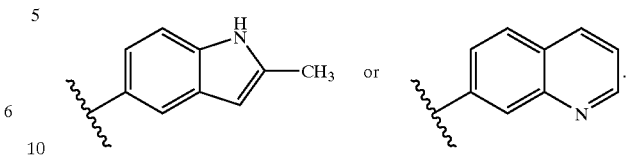

17. The compound of claim 16, wherein $R^{11}$ is —C(O)N$R^{12}R^{13}$ wherein $R^{12}$ and $R^{13}$ taken together with the nitrogen to which they are attached form a $C_1$–$C_{10}$ azabicyclic, aziridinyl, azetidinyl, or pyrrolidinyl ring wherein said $C_5$–$C_9$ azabicyclic, aziridinyl, azetidinyl, and pyrrolidinyl ring are optionally substituted by 1 to 5 $R^5$ substituents.

18. The compound of claim 17, wherein $R^{11}$ is —C(O)N$R^{12}R^{13}$ wherein $R^{12}$ and $R^{13}$ taken together with the nitrogen to which they are attached form a $C_5$–$C_9$ azabicyclic, azetidinyl or pyrrolidinyl ring wherein said $C_5$–$C_9$ azabicyclic, azetidinyl or pyrrolidinyl ring are optionally substituted by 1 to 5 $R^5$ substituents.

19. The compound of claim 18, wherein $R^{11}$ is —C(O)N$R^{12}R^{13}$ wherein $R^{12}$ and $R^{13}$ taken together with the nitrogen to which they are attached form a $C_5$–$C_9$ azabicyclic ring, wherein said $C_5$–$C_9$ azabicyclic ring is optionally substituted by 1 to 5 $R^5$ substituents.

20. The compound of claim 19, wherein $R^{11}$ is —C(O)N$R^{12}R^{13}$ wherein $R^{12}$ and $R^{13}$ taken together with the nitrogen to which they are attached form an azetidinyl ring, wherein said azetidinyl ring is optionally substituted by 1 to 5 $R^5$ substituents.

21. The compound of claim 20, wherein $R^{11}$ is —C(O)N$R^{12}R^{13}$ wherein $R^{12}$ and $R^{13}$ taken together with the nitrogen to which they are attached form a pyrrolidinyl ring, wherein said pyrrolidinyl ring is optionally substituted by 1 to 5 $R^5$ substituents.

* * * * *